US010316365B2

(12) United States Patent
Chute et al.

(10) Patent No.: US 10,316,365 B2
(45) Date of Patent: Jun. 11, 2019

(54) SIGNATURES OF RADIATION RESPONSE

(71) Applicant: DUKE UNIVERSITY, Durham, NC (US)

(72) Inventors: John Chute, Durham, NC (US); Joseph Nevins, Durham, NC (US); Holly Dressman, Durham, NC (US); Nelson Chao, Durham, NC (US)

(73) Assignee: Duke University, Durham, NC (US)

( * ) Notice: Subject to any disclaimer, the term of this patent is extended or adjusted under 35 U.S.C. 154(b) by 446 days.

(21) Appl. No.: 14/092,291

(22) Filed: Nov. 27, 2013

(65) Prior Publication Data

US 2014/0243226 A1 Aug. 28, 2014

Related U.S. Application Data

(63) Continuation of application No. 12/736,393, filed as application No. PCT/US2009/002048 on Apr. 2, 2009, now abandoned.

(60) Provisional application No. 61/064,904, filed on Apr. 2, 2008.

(51) Int. Cl.
 C12Q 1/68 (2018.01)
 C12Q 1/6881 (2018.01)
 C12Q 1/6876 (2018.01)

(52) U.S. Cl.
 CPC ......... *C12Q 1/6881* (2013.01); *C12Q 1/6876* (2013.01); *C12Q 2600/158* (2013.01)

(58) Field of Classification Search
 None
 See application file for complete search history.

(56) References Cited

U.S. PATENT DOCUMENTS

| 8,080,377 B2 | 12/2011 | Ryu et al. | |
| 2008/0176755 A1* | 7/2008 | Amundson | B01L 3/5027 506/7 |
| 2009/0023149 A1 | 1/2009 | Knudsen | |
| 2009/0062196 A1 | 3/2009 | D'Andrea et al. | |
| 2011/0028338 A1 | 2/2011 | Chute et al. | |

FOREIGN PATENT DOCUMENTS

| KR | 10-2009-0034011 | 4/2009 |
| KR | 10-2009-0121842 | 11/2009 |
| WO | 2008/082712 | 7/2008 |
| WO | 2014/046706 | 3/2014 |

OTHER PUBLICATIONS

Rieger et al. (Nucleic Acids Research 2004, 32(16):4786-4803), IDS reference.*
Rus et al. (Clinical Immunology, 2002, 102(3):283-290), IDS reference.*
Dressman et al. (PLoS Medicine, 2007, 4(4):e106, p. 690-701; published Apr. 3, 2007), IDS reference.*
Agilent 44k annotation list, 2018, 5080 pages from txt file on Agilent gene list website (Year: 2018).*
Agilent website obtained from https://www.chem.agilent.com/cag/bsp/gene_lists.asp, p. 1-2 (Year: 2018).*
International Search Report and Written Opinion for International Patent Application No. PCT/US2013/000218 dated Dec. 11, 2013 (9 pages).
International Preliminary Report on Patentability for International Patent Application No. PCT/US2013/000218 dated Mar. 24, 2015 (7 pages).
Office action in U.S. Appl. No. 12/736,393 dated May 28, 2013 (18 pages).
Amundson, S.A. et al., "Human in vivo radiation-induced biomarkers: Gene expression changes in radiotherapy patients," Cancer Research (2004) 64:6368-6371.
Dressman, H.K. et al., "Gene expression signatures that predicts radiation exposure in mice and humans," PLOS Medicine (2007) 4(4):e106 doi:10.1371/journal.pmed.0040106.
Fiala, M. et al., "Innate immunity and transcription of MGAT-III and Toll-like receptors in Alzheimer's disease patients are improved by bisdemethoxycurcumin," PNAS (2007) 104(31):12849-12854.
Lee, Y.-S., et al., "Radiation induced gene expression profiling in dorsal skin tissue of hairless mouse," Korean Journal of Investigative Dermatology (2007) 14(1):10-16.
Rieger, K.E. et al., "Portrait of transcriptional responses to ultraviolet and ionizing radiation in human cells," Nucleic Acids Research (2004) 32(16):4786-4803.
Rockett, J.C. et al., "Surrogate tissue analysis: Monitoring toxicant exposure and health status of inaccessible tissues through the analysis of accessible tissues and cells," Toxicology and Applied Pharmacology (2004).
Rus, V. et al., Expression of cytokine- and chemokine-related genes in peripheral blood mononuclear cells from lupus patients by cDNA array, Clinical Immunology (2002) 102(3)283-290 (Abstract).
International Search Report and Written Opinion for International Patent Application No. PCT/US2009/002048 dated Dec. 2, 2009 (13 pages).
International Preliminary Report on Patentability for International Patent Application No. PCT/US2009/002048 dated Oct. 14, 2010 (7 pages).
Fiala et al, "Innate immunity and transcription of MGAT-III and Toll-like receptors in Alzheimer's disease patients are improved by bisdemethoxycurcumin", PNAS 104(31):12849-14854 (2007).
Rieger et al, "Portrait of transcriptional responses to ultraviolet and ionizing radiation in human cells", Nucleic Acids Research 32(16):4786-4803(2004).
Rus et al, "Expression of cytokine- and chemokine-related genes in peripheral blood mononuclear cells from lupus patients by cDNA array", Clinical Immunology 102(3):283-290 (2002).

(Continued)

*Primary Examiner* — Stephanie K Mummert
(74) *Attorney, Agent, or Firm* — Quarles & Brady LLP

(57) ABSTRACT

The present invention relates, in general, to gene expression profiles, and in particular, to a peripheral blood gene expression profile of an environmental exposure, ionizing radiation. The invention further relates to methods of screening patients for radiation exposure based on gene expression profiling and to kits suitable for use in such methods.

13 Claims, 11 Drawing Sheets

(56) References Cited

OTHER PUBLICATIONS

Dressman et al, "Gene Expression Signatures That Predict Radiation Exposure in Mice and Humans", PloS Medicine 4(4) :e106, p. 690-701 published Apr. 3, 2007.
Amundson et al, "Human In vivo Radiation-Induced Biomarkers: Gene Expression Changes in Radiotherapy Patients", Cancer Res. 64:6368-6371 (2004).

* cited by examiner

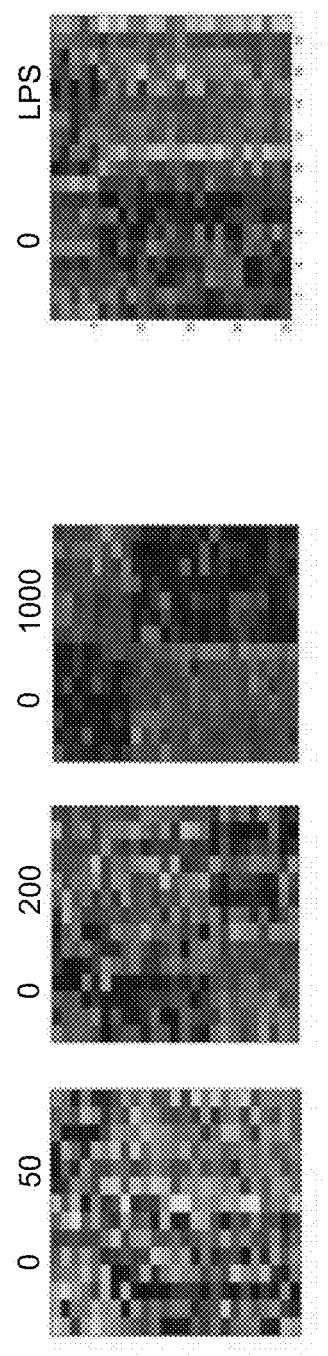

SIGNATURES OF RADIATION RESPONSE

This application is a continuation of U.S. application Ser. No. 12/736,393, filed 4 Oct. 2010, which is the U.S. national phase of International Application No. PCT/US2009/002048, filed 2 Apr. 2009, which designated the U.S. and claims the benefit to U.S. Provisional Application No. 61/064,904, filed 2 Apr. 2008, the entire contents of each of which are hereby incorporated by reference.

This invention was made with government support under Grant No. AI-06779801 awarded by the National Institutes of Health. The government has certain rights in the invention.

TECHNICAL FIELD

The present invention relates, in general, to gene expression profiles, and in particular, to a peripheral blood gene expression profile of an environmental exposure, ionizing radiation. The invention further relates to methods of screening patients for radiation exposure based on gene expression profiling and to kits suitable for use in such methods.

BACKGROUND

Invasive procedures are often required for accurate screening and diagnosis of common medical conditions (Boolchand et al, Ann. Intern. Med. 145:654-659 (2006)). Examination of the peripheral blood often suffices to establish certain diagnoses, such as chronic lymphocytic leukemia (Damle et al, Blood Epub Ahead of Print (2007)), which afflicts the circulating lymphocyte directly. Measurement of total white blood cell counts and the WBC differential (e.g. neutrophils, lymphocytes, monocytes) is routinely performed in medical practice and can facilitate many diagnoses (e.g. bacterial or viral infection). Recently, it has been suggested that gene expression profiling of peripheral blood cells, particularly lymphocytes, can serve as sensitive tool to assess for the presence of certain diseases, such as systemic lupus erythematosus, rheumatoid arthritis, neurologic disease, viral and bacterial infections, breast cancer, atherosclerosis and environmental exposures, including tobacco smoke (Mandel et al, Lupus 15:451-456 (2006), Heller et al, Proc. Natl. Acad. Sci. USA 94:2150-2155 (1997), Edwards et al, Mol. Med. 13:40-58 (2007), Baird, Stroke 38:694-698 (2007), Rubins et al, Proc. Natl. Acad. Sci. USA 101:15190-15195 (2004), Martin et al, Proc. Natl. Acad. Sci. USA 98:2646-2651 (2001), Patino et al, Proc. Natl. Acad. Sci. USA 102:3423-3428 (2005), Lampe et al, Cancer Epidemiol. Biomarkers Prev. 13:445-453 (2004), Ramilo et al, Blood 109:2066-2077 (2007)). Results from these studies suggest that patterns of gene expression within circulating PB cells can distinguish individuals afflicted by these conditions from those who are not (Mandel et al, Lupus 15:451-456 (2006), Heller et al, Proc. Natl. Acad. Sci. USA 94:2150-2155 (1997), Edwards et al, Mol. Med. 13:40-58 (2007), Baird, Stroke 38:694-698 (2007), Rubins et al, Proc. Natl. Acad. Sci. USA 101:15190-15195 (2004), Martin et al, Proc. Natl. Acad. Sci. USA 98:2646-2651 (2001), Patino et al, Proc. Natl. Acad. Sci. USA 102:3423-3428 (2005), Lampe et al, Cancer Epidemiol. Biomarkers Prev. 13:445-453 (2004), Ramilo et al, Blood 109:2066-2077 (2007)). It has, therefore, been suggested that PB gene expression profiling has potential utility in the screening for diseases and environmental exposures.

Any consideration of applying PB gene expression profiles for the detection of disease or environmental exposures requires a determination of the impact of PB cellular composition, time, gender, and genotype on PB gene expression (Lampe et al, Cancer Epidemiol. Biomarkers Prev. 13:445-453 (2004), Ramilo et al, Blood 109:2066-2077 (2007), Whitney et al, Proc. Natl. Acad. Sci. USA 101:1896-1901 (2003), Yan et al, Science 297:1143 (2002)). Additionally, it is unclear whether PB gene expression profiles that have been associated with various medical conditions are specific for that phenotype, or rather reflect a generalized response to genotoxic stress. Examination of the specificity of PB gene expression profiles in response to different stimuli and the durability of these signatures over time is critical to the translation of this strategy into clinical practice.

Ionizing radiation represents a particularly important environmental hazard, which, at lowest dose exposures, causes little acute health effects (Kaiser, Science 302:378 (2003)) and, at higher dose exposures, can cause acute radiation syndrome and death (Wasalenko et al, Ann. Int. Med. 140:1037-1051 (2004), Mettler et al, N. Engl. J. Med. 346:1554-1561 (2002), Dainiak, Exp. Hematol. 30:513-528 (2002)). Numerous studies have been performed to attempt to understand the biologic effects of ionizing radiation in humans. Specific mutations in p53 and HPRT have been identified in somatic cells from survivors of the Hiroshima and Nagasaki atomic bombings (Iwamoto et al, J. Natl. Canc. Inst. 90:1167-1168 (1998), Hirai et al, Mutant Res. 329:183-196 (1995), Takeshima et al, Lancet 342:1520-1521 (1993), Neel et al, Annu. Rev. Genet. 24:327-362 (1990)).

Gene expression analyses have been performed on human tumor cells, cell lines, and peripheral blood from small numbers of irradiated patients in order to identify specific genes that are involved in the response to radiation injury (Jen et al, Genome Res. 13:2092-2100 (2003), Amundson et al, Radiat. Res. 154:342-346 (2000), Amundson et al, Radiat. Res. 156:657-661 (2001), Falt et al, Carcinogenesis 24:1837-1845 (2003), Amundson et al, Cancer Res. 64:6368-6371 (2004)). Recently, public health focus has centered on the development of capabilities to accurately screen large numbers of people for radiation exposure in light of the anticipated use of radiological or nuclear materials by terrorists to produce "dirty bombs" or "improvised nuclear devices" (Wasalenko et al, Ann. Int. Med. 140:1037-1051 (2004), Mettler et al, N. Engl. J. Med. 346:1554-1561 (2002), Dainiak, Exp. Hematol. 30:513-528 (2002)).

A method of screening humans for environmental exposure has been suggested. This method relies on the identification of patterns of gene expression, or metagenes in PB cells that accurately distinguish between irradiated and non-irradiated individuals (Dressman et al, PLoS Med. 4:690-701 (2007)). Metagenes can be identified in the PB that distinguish different levels of exposure with an accuracy of 96% (Dressman et al, PLoS Med. 4:690-701 (2007)).

The present invention results, at least in part, from studies designed to evaluate the specificity of PB gene expression signatures and to determine the influence of genetic variation and time on the performance of the signature. The results of these studies indicate that this approach represents a viable strategy for identifying environmental exposures and one that can be employed for screening populations of affected individuals.

SUMMARY OF THE INVENTION

The present invention relates generally to gene expression profiles. More specifically, the invention relates to PB gene expression profile of an environmental exposure, ionizing radiation. The invention further relates to a method of screening patients for radiation exposure based on gene expression profiling and to kits suitable for use in such methods.

Objects and advantages of the present invention will be clear from the description that follows.

BRIEF DESCRIPTION OF THE DRAWINGS

(FIG. 1B) A graph of the predicted capabilities of the irradiation signature across all mice (including C57Bl6 and BALB/c strains, males and females and 3 sampling time points) versus a control, non irradiated sample. All predicted probabilities for the controls are listed.

(FIG. 2B) Heat map images illustrating expression pattern of genes found in the female C57Bl6 strain or male C57Bl6 strain predicting the irradiation status of the opposite sex at dosage 50 cGy, 200 cGy, 1000 cGy. High expression is depicted as red, and low expression is depicted as blue. (FIG. 2C) A leave-one-out cross-validation analysis of the classification for control (blue) versus 50 cGy (black), 200 cGy (green), and 1000 cGy (red) for the female C57Bl6 (squares) and male C57Bl6 (circles) samples is shown. The control probabilities for each prediction are shown.

(FIG. 3A) Heat map images illustrating expression pattern of genes selected for classifying control, non-irradiated samples versus 50 cGy, 200 cGy, 1000 cGy irradiated samples between female C57Bl6 strain (top) and female BALB/c strain (bottom). (FIG. 3B) Heat map images illustrating expression pattern of genes developed in one strain as predicting the other strain (C57Bl6 or BALB/c). High expression is depicted as red and low expression is depicted as blue. (FIG. 3C) A leave-one-out cross-validation analysis of the classification for control versus 50 cGy (black), 200 cGy (green), and 1000 cGy (red) for the female BALB/c (open-circles) and female C57Bl6 (closed circles) samples is shown. The control probabilities for each prediction are shown. BK represents the application of female C57Bl6 metagenes to predict the status of female BALB/c mice, and BC represents using female BALB/c mice metagenes to predict the status of female C57Bl6 mice.

(FIG. 4A) Heat map images illustrating expression pattern of genes selected for classifying control, non-irradiated samples versus 50 cGy, 200 cGy, 1000 cGy irradiated samples at time points 6 hr, 24 hr, and 7 days. (FIG. 4B) Heat map images illustrating expression pattern of genes found in the 6 hr time point as applied to the dosages 50 cGy, 200 cGy, 1000 cGy at 24 hr and 7 day time points. High expression is depicted as red, and low expression is depicted as blue. (FIG. 4C) A leave-one-out cross-validation analysis of the classification for control (blue) versus 50 cGy (black), 200 cGy (green), and 1000 cGy (red) for the time points 6 hr (circles), 24 hr (squares), and 7 days (triangles) is shown. The control probabilities for each prediction are shown.

FIGS. 5A and 5B. Peripheral blood profiles of irradiation and LPS-treatment are highly specific. (FIG. 5A) Heat maps representing unique metagene profiles are shown which were utilized to distinguish 3 different levels of irradiation (left) and to distinguish LPS-treatment (right) in C57Bl6 mice. (FIG. 5B) The graph at left represents the predictive capabilities of the PB irradiation signatures in the female C57Bl6 mice in predicting dosage profiles at 50 cGy (black), 200 cGy (green), and 1000 cGy (red); the middle graph represents the predictive capabilities of the irradiation signatures when validated against the LPS-treated samples (squares); at right, the LPS signature was validated against the C57Bl6 irradiated mice and the predicted probabilities for 50 cGy (black), 200 cGy (green), and 1000 cGy (red) are shown.

(FIG. 6A) The heat map on the left depicts the expression profiles of genes (rows) selected to discriminate the human samples (columns); high expression is depicted as red, and low expression is depicted as blue. A leave-one-out cross-validation assay (FIG. 6C) demonstrated that the PB metagene of radiation was capable of distinguishing healthy donors (black), non-irradiated patients (gray), irradiated patients (red), pre-chemotherapy treatment patients (green), and post-chemotherapy patients (blue). A ROC curve analysis was used to define a cut-off for sensitivity and specificity of the predictive model of radiation. The dotted line represents this threshold of sensitivity and specificity. (FIG. 6B) The heatmap on the left depicts an expression profile of chemotherapy treatment that distinguishes chemotherapy-treated versus untreated patients. A leave-one-out cross-validation assay (FIG. 6D) demonstrated that this PB metagene of chemotherapy treatment could accurately distinguish pre-chemotherapy patients (green), chemotherapy-treated patients (blue), healthy individuals (black), pre-irradiated patients (gray) and irradiated patients (red).

DETAILED DESCRIPTION OF THE INVENTION

Figure 1A:
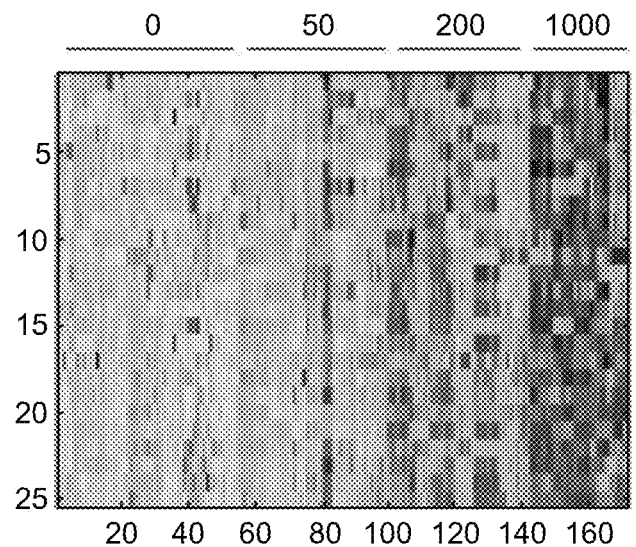
FIGS. 1A and 1B. Peripheral blood gene expression profiles distinguish irradiated mice within a heterogeneous population (FIG. 1A) A heat map of a 25 gene profile that can predict radiation status. The figure is sorted by dosage (0 cGy, 50 cGy, 200 cGy, and 1000 cGy). High expression is depicted as red, and low expression is depicted as blue.

The present invention results, at least in part, from the demonstration that exposure to ionizing radiation induces a pronounced and characteristic alteration in PB gene expression. The PB expression profile disclosed herein provides basis for a method of screening a heterogeneous human population, for example, in the event of a radiological or nuclear event.

A gene expression profile that distinguishes radiation status in humans is set forth in Table 7. As described in the Example that follows, a supervised binary regression analysis identified this metagene profile of 25 genes that can be used to distinguish irradiated from non-irradiated individuals. The PB samples used to establish the profile in Table 7 were collected 6 hours following irradiation (see Table 6 for details of exposure).

The invention relates to a method screening patients for radiation exposure by collecting PB from the patients and isolating mononuclear cells therefrom. RNA can be extracted from the mononuclear cells using standard techniques, including those described in the Example below. The extracted RNA can be amplified and suitable probes prepared (see Example and Dressman et al, PLoS Med. 4:690-701 (2007)). Gene expression levels can then be determined using, for example, microarray techniques (see Example and Dressman et al, PLoS Med. 4:690-701 (2007)).

A patient that displays the gene expression profile set forth in Table 7 is a patient that has been exposed to radiation (e.g., about 6 hours prior to PB collection). While the 25 genes set forth in Table 7 constitute one signature suitable for use is distinguishing radiation status, the invention also includes methods based on the use of signatures comprising the following: H200000088, H200008365, H200011577, H200014719, H200016323, H300000421, H300003103, H300010830, H300015667, H300019371, H300020858, H300021118, H300022025. Other subsets of the signature set forth in Table 7 (e.g., comprising at least 5 or at least 10 genes) are potentially suitable for use in accordance with the present invention.

While the PB expression profile described herein is highly predictive of radiation status, sex differences can contribute to characteristically distinct PB molecular responses to radiation, for example at low exposure levels (e.g., about 50 cGy). Accordingly, use of gender specific assays can be advantageous, for example, at low levels of exposure.

As shown in the Example that follows, the time of PB collection following radiation exposure does not significantly impact the accuracy of PB signatures to predict radiation status or distinguish different levels of exposure. While time as a single variable does not lessen the accuracy in distinguishing irradiated from non-irradiated individuals, the content of the genes which comprise the PB signature can change as a function of time. Thus, while PB predictors of radiation exposure can change over time, PB signatures can continuously be identified (e.g., through 7 days) that are highly accurate at predicting radiation status and distinguishing different levels of exposure.

The invention also relates to reagents and kits suitable for use in practicing the above-described methods. Kit components can vary, however, examples of components include an array probe of nucleic acids in which the genes listed in Table 7, or subset thereof, are represented. A variety of different array formats or known in the art with a variety of probe structures, subset components and attachment technologies. Representative array structures include those described in U.S. Pat. Nos. 5,143,854; 5,288,644; 5,342,633; 5,432,049; 5,470,710; 5,492,806; 5,503,980; 5,510,270; 5,525,464; 5,547,839; 5,580,732; 5,661,028; 5,800,992; WO 95/21265; WO 96/31622; WO 97/10365; WO 97/27317; EP 373203 and EP 785280 (see also U.S. Published Appln. No. 20060141493). Kits of the invention can also include specific primers designed to selectively amplify the genes in Table 7, or subset thereof. Gene specific primers and methods of using same are described in U.S. Pat. No. 5,994,076. The kits can also include additional reagents, e.g., dNTPs and/or rNTPs, buffers, enzymes, etc.

Certain aspects of the invention can be described in greater detail in the non-limiting Example that follows. (See also Dressman et al, PLoS Med. 4:690-701 (2007)).

EXAMPLE

Experimental Details

Murine Irradiation Study

Ten to 11 week old male and female C57Bl6 and female BALB/c mice (Jackson Laboratory, Bar Harbor, Me.) were housed at the Duke Cancer Center Isolation Facility under regulations approved by the Duke University Animal Care and Use Committee. Between 5-10 mice/group were given total body irradiation (TBI) with a Cs137 source at an average of 660 cGy/min at doses of 50, 200, or 1000 cGy as previously described (Dressman et al, PLoS Med. 4:690-701 (2007)). Six hours, 24 hours, or 7 days post-TBI, approximately 500 µl peripheral blood was collected by retro-orbital bleed from both irradiated and control mice. PB mononuclear cells (PB MNCs) were isolated for total RNA extractions. Total RNA was extracted with Qiagen RNAeasy Mini Kits as previously described (Dressman et al, PLoS Med. 4:690-701 (2007)). RNA quality was assayed using an Agilent Bioanalyzer 2100 (Agilent Technologies, Inc., Palo Alto, Calif.).

Murine LPS Study

Ten C57Bl6 female mice were given intraperitoneal injections of a 100 µg of lipopolysaccharide endotoxin (LPS) from E. coli 055:B5 (Sigma-Aldrich, St. Louis, Mo.) to induce sepsis syndrome as previously described (Hick et al, J. Immunol. 177:169-176 (2006)). Peripheral blood was collected 6 h later from treated and control mice, and RNA was processed as described in the irradiation studies.

Human Irradiation and Chemotherapy Treatment Studies

With approval from the Duke University Institutional Review Board (IRB), between 5-12 mL of peripheral blood was collected from patients prior to and 6 hrs following total body irradiation with 150 to 200 cGy as part of their pre-transplantation conditioning (Dressman et al, PLoS Med. 4:690-701 (2007)). For additional comparison, peripheral blood was obtained from healthy volunteers and an additional cohort of patients prior to and 6 hrs following the initiation of alkylator-based chemotherapy alone (without radiotherapy). All patients and healthy volunteers who participated in this study provided written informed consent prior to enrollment, as per the Duke IRB guidelines. PB MNCs and total RNA were isolated from the blood using the identical methods as described for collection of murine cells and RNA.

DNA Microarrays

Mouse and human oligonucleotide arrays were printed at the Duke Microarray Facility using Operon's Mouse Genome Oligo sets (version 3.0 and version 4.0) and Operon's Human Genome Oligo set (version 3.0 and version 4.0). Data generated from Operon's Mouse and Human version 3 was previously described (Dressman et al, PLoS Med. 4:690-701 (2007)). Operon's Mouse Genome Oligo set (version 4.0) (https://www.operon.com/arrays/oligosets_mouse.php) contains 35,852 oligonucleotide probes representing 25,000 genes and approximately 38,000 transcripts. Operon's Human Genome Oligo set (version 4.0) (https://www.operon.com/arrays/oligosets_human.php) contains 35,035 oligonucleotide probes, representing approximately 25,100 unique genes and 39,600 transcripts. In order to compare across versions of the Operon oligo sets, Operon provided a map that matched the probes from both versions and only those oligonucleotides that overlapped between versions 3.0 and 4.0 were used in the analysis.

RNA and Microarray Probe Preparation and Hybridization

Briefly, MNCs were pelleted, and total RNA was isolated using the RNAeasy mini spin column (Dressman et al, PLoS Med. 4:690-701 (2007)). Total RNA from each sample (mouse or human) and the universal reference RNA (Universal Human or Mouse Reference RNA, Stratagene, http://www.stratagene.com) were amplified and used in probe preparation as previously described (Dressman et al, PLoS Med. 4:690-701 (2007)). The sample (mouse or human) was labeled with Cy5 and the reference (mouse or human) was labeled with Cy3. The reference RNA allows for the signal for each gene to be normalized to its own unique factor allowing comparisons of gene expression across multiple samples. This serves as a normalization control for two-color microarrays and an internal standardization for the arrays. Amplification, probe preparation and hybridization protocols were performed as previously described (Dressman et al, PLoS Med. 4:690-701 (2007)) and each condition examined had multiple replicates analyzed (n=3-18 per mouse condition and n=18-36 per human condition). Detailed protocols are available on the Duke Microarray Facility web site (http://microarray.genome.duke.edu/services/spotted-arrays/protocols).

Data Processing and Statistical Analysis

Genespring GX 7.3 (Agilent Technologies) was used to perform initial data filtering in which spots whose signal intensities below 70 in either the Cy3 or Cy5 channel were removed. For each analysis, only those samples in that analysis were used in the filtering process. To compare data from previously published results (Dressman et al, PLoS Med. 4:690-701 (2007)), only those probes were used that mapped to each other across the version 3.0 and version 4.0 arrays. To then account for missing values, PAM software (http://www-stat.stanford/edu/~tibs/PAM/) was used to impute missing values. k-nearest neighbor was used where missing values were imputed using a k-nearest neighbor average in gene space. In the analysis approach in which all samples were included, lowess normalization of the data followed by batch effect removal using 2-way mixed model ANOVA (Partek Incorporated) was performed. Gene expression profiles of dose response were used in a supervised analysis using binary regression methodologies as described previously (Dressman et al, PLoS Med. 4:690-701 (2007)). Prediction analysis of the expression data was performed using MATLAB software as previously described (Dressman et al, PLoS Med. 4:690-701 (2007)). When predicting levels of radiation exposure, gene selection and identification is based on training the data and finding those genes most highly correlated to response. Each signature summarizes its constituent genes as a single expression profile and is here derived as the first principal component of that set of genes (the factor corresponding to the largest singular value), as determined by a singular value decomposition. Given a training set of expression vectors (of values across metagenes) representing two biological states, a binary probit regression model is estimated using Bayesian methods. Bayesian fitting of binary probit regression models to the training data then permits an assessment of the relevance of the metagene signatures in within-sample classification, and estimation and uncertainty assessments for the binary regression weights mapping metagenes to probabilities of radiation exposure. To internally validate the predictive capacity of the metagene profiles, leave-one-out cross validation studies were performed as previously described (Dressman et al, PLoS Med. 4:690-701 (2007)). A leave one out cross validation involves removing one sample from the dataset, using the remaining samples to develop the model, and then predicting the status of the held out sample. This is then repeated for each sample in the dataset. This approach was utilized as previously described (Dressman et al, PLoS Med. 4:690-701 (2007)). A ROC curve analysis was used to define a cut-off for sensitivity and specificity in the predictive models of radiation. Genes found to be predictive of radiation dose were characterized utilizing an in-house program, GATHER (http://meddb01.duhs.duke.edu/qather/). GATHER quantifies the evidence supporting the association between a gene group and an annotation using a Bayes factor (Pournara et al, BMC Bioinformatics 23:1-20 (2007)). All microarray data files can be found at http://data.cgt.duke.edu/ChuteRadiation.php and at gene expression omnibus website (GEO [http://www.ncbi.nlm.nih.gov/geo], accession number GSE10640).

Results

Figure 1B:
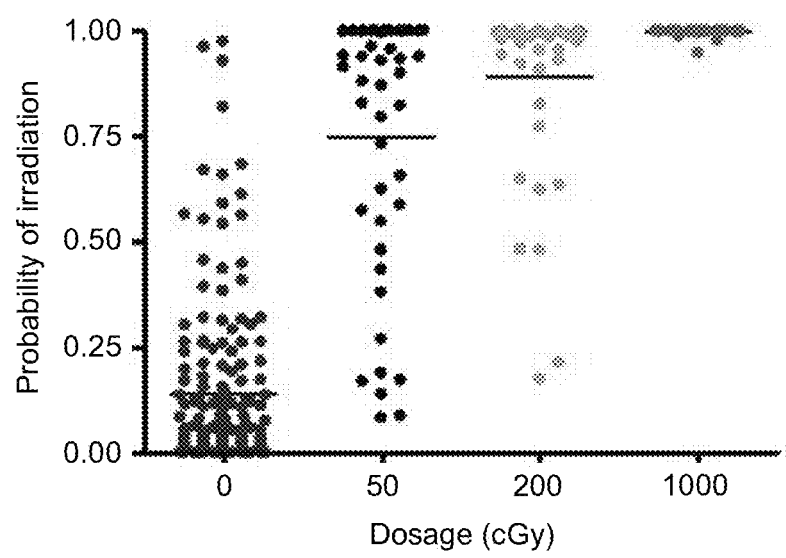

PB Gene Expression Signatures Predict Ionizing Radiation Exposure in a Heterogeneous Population In a previous study, it was demonstrated that PB collected from a single strain and gender of mice, at a single time point, contained patterns of gene expression that predicted both prior radiation exposure and distinguished different levels of radiation exposure with a high degree of accuracy (Dressman et al, PLoS Med. 4:690-701 (2007)). In this study, a determination was made as to whether PB gene expression signatures could be identified that predict radiation exposure status within a population that was heterogeneous for genotype, gender and time of sampling. It was found that a clear pattern of gene expression could be identified within this heterogeneous population of mice that distinguished non-irradiated animals from those irradiated with 50 cGy, 200 cGy, and 1000 cGy (FIG. 1A). To verify that these patterns did indeed represent genes reflecting exposure to radiation, a leave-one-out cross-validation analysis was used to assess the ability of the pattern to predict the relevant samples (FIG. 1B). The results demonstrate that the pattern selected for distinguishing control animals from those irradiated at various doses has the capacity to predict the status of the samples. The accuracies of prediction of the non-irradiated samples, the 50 cGy-, 200 cGy- and 1000 cGy-irradiated samples were 92%, 78%, 91% and 100%, respectively.

Sex Differences Impact the Accuracy of Gene Expression Signatures of Radiation

Figure 2A:
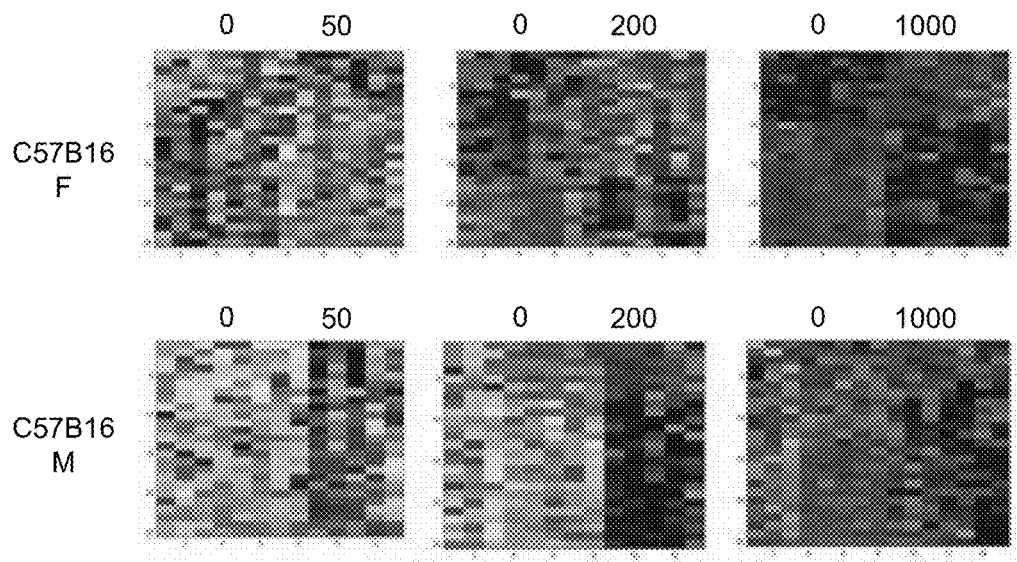
FIGS. 2A-2C. Impact of sex on murine irradiation profiles (FIG. 2A) Heat map images illustrating expression pattern of genes selected for classifying control, non-irradiated mice versus 50 cGy, 200 cGy, or 1000 cGy irradiated mice within female (top) and male C57Bl6 mice (bottom).
Figure 2B:
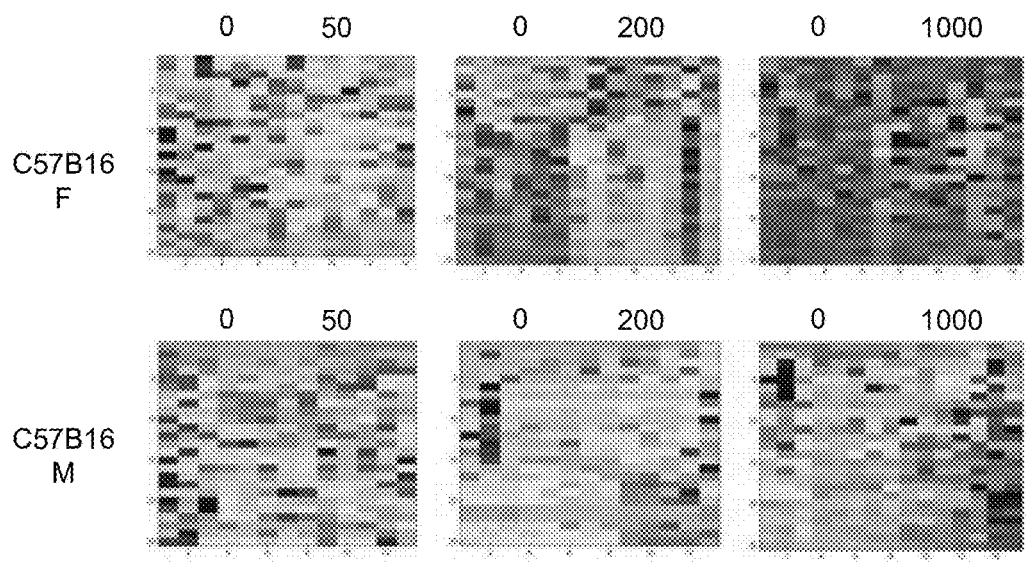
Figure 2C:
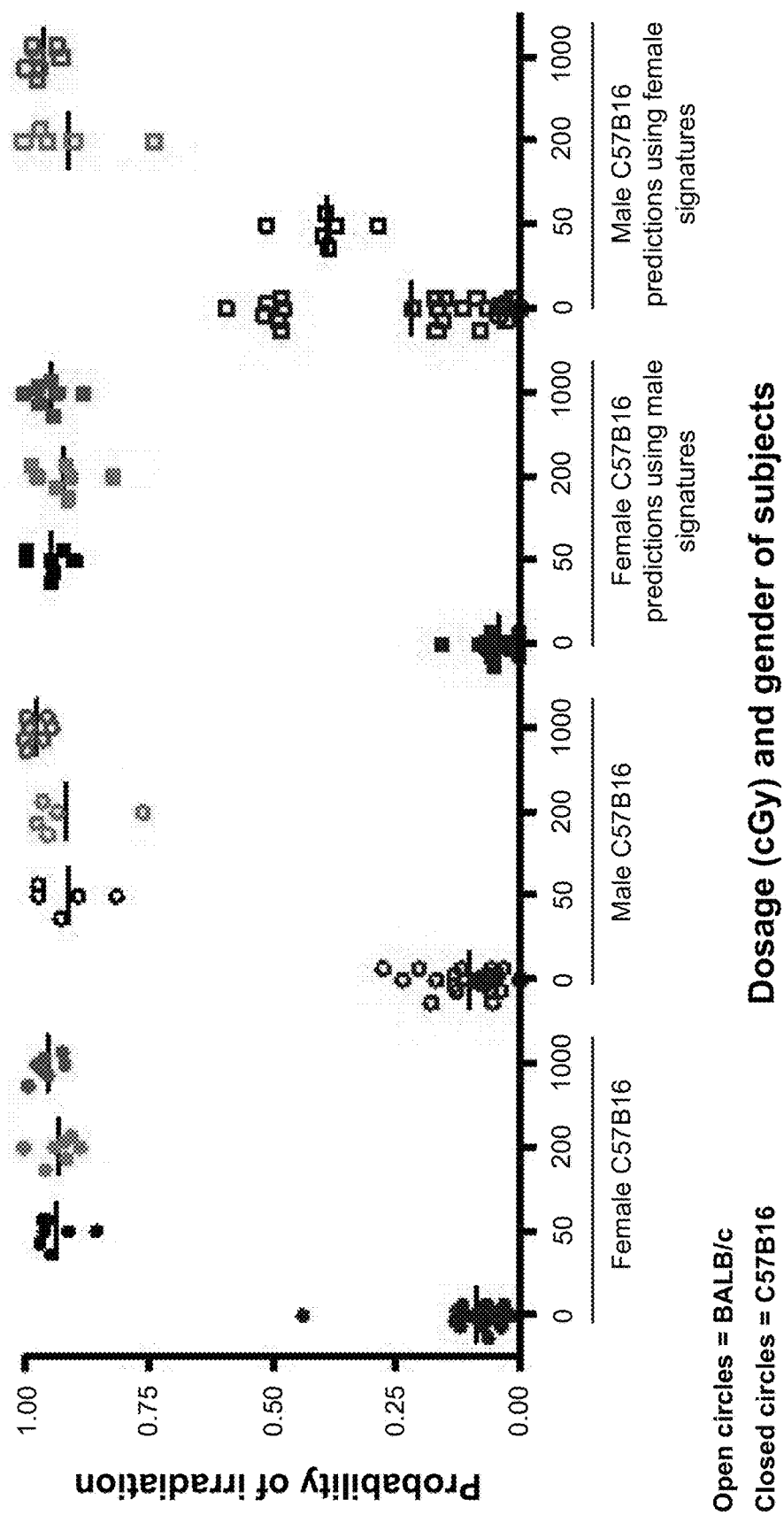

A determination was then made as to the extent to which variables within a heterogeneous population can limit the accuracy of PB gene expression profiling. In order to address the impact of sex difference, healthy adult male and female C57Bl6 mice were irradiated with 50 cGy, 200 cGy, and 1000 cGy and PB was collected at 6 hours post-irradiation, along with PB from non-irradiated control mice (n=7-10 per group). Patterns of gene expression could be identified in the PB of both male and female mice that appeared to distinguish radiation exposure status (FIG. 2A). When the PB signatures from the male C57Bl6 mice were tested against the female PB samples, the heat map analysis suggested less distinction between the non-irradiated and irradiated profiles (FIG. 2B). Comparable effects were observed when the female PB signatures were applied against male PB samples. A leave-one-out cross-validation analysis demonstrated that the male and female PB signatures of radiation were 100% accurate in predicting the radiation status of PB samples from mice of the same sex (FIG. 2C). The male PB signatures also were 100% accurate in predicting the status of the female mice. However, the female PB signatures were less accurate in distinguishing the non-irradiated from 50 cGy irradiated male mice, with improved accuracy in predicting non-irradiated samples from male mice irradiated with higher doses of radiation (200 cGy and 1000 cGy; FIG. 2C). The basis for the observed differences in predicting the radiation status of mice across gender differences may be a function of the distinct sets of genes which are represented in the predictors of radiation exposure in males and females (Table S1). Less than 15% of the genes overlapped between the PB metagenes of males and females at each dose of radiation.

TABLE 1

Genes that distinguish radiation responses in male and female C57B16 mice. Operon Oligo ID can be queried in the OMAD database (http://omad.operon.com)

| Operon OligoID | Gene Symbol | RefSeq | Genbank | Description |
|---|---|---|---|---|
| | MALES |
| | 50 Gy |
| M200013484 | 9030617O03Rik | NM_145448 | BC021385 | — |
| M200000800 | Ccng1 | NM_009831 | AB005559 | CYCLIN G1 (CYCLIN G] |
| M200004687 | Dda3-pending | NM_019976 | AK041835 | DIFFERENTIAL DISPLAY AND ACTIVATED BY P53; P53-REGULATED DDA3. |
| M200003784 | Bax | NM_007527 | L22472 | APOPTOSIS REGULATOR BAX, MEMBRANE ISOFORM ALPHA. |
| M200007794 | Wig1 | NM_009517 | AF012923 | WILD-TYPE P53-INDUCED GENE 1. |
| M200016031 | Polk | NM_012048 | AB040764 | POLYMERASE (DNA DIRECTED), KAPPA; DINB HOMOLOG 1 (*E. COLI*); DNA DAMAGE-INDUCIBLE PROETIN B; DNA DAMAGE-INDUCIBLE PROTEIN B; POLYMERASE (DNA DIRECTED) KAPPA. |
| M200000935 | Gcdh | NM_008097 | U18992 | GLUTARYL-COA DEHYDROGENASE, MITOCHONDRIAL PRECURSOR (EC 1.3.99.7) (GCD). |
| M300010491 | D030041N15Rik | NM_153416 | BC018191 | ALADIN (ADRACALIN).] |
| M200003481 | 2210412K09Rik | NM_029814 | BC006947 | — |
| M200006137 | Stinp | NM_021897 | AY034612 | STRESS INDUCED PROTEIN; THYMUS EXPRESSED ACIDIC PROTEIN. |
| M300008376 | Pon2 | NM_008896 | L48514 | SERUM PARAOXONASE/ARYLESTERASE 2 (EC 3.1.1.2) (EC 3.1.8.1) (PON 2) (SERUM ARYLDIAKYLPHOSPHATASE 2) (A-ESTERASE 2) (AROMATIC ESTERASE 2).] |
| M200006229 | Dstn | NM_019771 | AB025406 | DESTRIN (ACTIN-DEPOLYMERIZING FACTOR) (ADF). |
| M300013831 | Myo15 | NM_010862 | AB014510 | MYOSIN XV (UNCONVENTIONAL MYOSIN-15). |
| M200009374 | 2310045N01Rik | NM_008578 | AK009829 | MYOCYTE-SPECIFIC ENHANCER FACTOR 2B. |
| M200015906 | 5530601I19Rik | NM_027797 | BC022756 | — |
| M200004993 | Ifi47 | NM_008330 | M63630 | INTERFERON GAMMA INDUCIBLE PROTEIN; INTERFERON GAMMA INDUCIBLE PROTEIN, 47 KDA |
| M200006667 | D11Ertd619e | NM_026538 | AK011136 | PROBABLE ATP-DEPENDENT 61 KDA NUCLEOLAR RNA HELICASE. |
| M200013613 | Gnrpx-pending | — | BC005565 | — |
| M300020474 | — | — | — | — |
| M200004237 | Ris2 | NM_026014 | AK028287 | RETROVIRAL INTEGRATION SITE 2; RETROVIRAL INTEGRATION SITE 1. |
| M200005712 | Hexb | NM_010422 | U07741 | BETA-HEXOSAMINIDASE BETA CHAIN PRECURSOR (EC 3.2.1.52) (N-ACETYL-BETA-GLUCOSAMINIDASE) (BETA-N-ACETYLHEXOSAMINIDASE) (HEXOSAMINIDASE B). |
| M200000599 | Pps | NM_008916 | AK054436 | PUTATIVE PHOSPHATASE; PI-5-PHOSPHATASE RELATED; PUTATIVE PI-5-PHOSPHATASE. [ |
| M200014192 | — | NM_053193 | AF322193 | CLEAVAGE AND POLYADENYLATION SPECIFICITY FACTOR, 160 KDA SUBUNIT (CPSF 160 KDA SUBUNIT). |
| M200004343 | 4833412N02Rik | NM_029020 | AK030624 | — |
| M200002381 | Fanca | NM_016925 | AF178934 | FANCONI ANEMIA, COMPLEMENTATION GROUP A. |
| | 200 Gy |
| M200013484 | 9030617O03Rik | NM_145448 | BC021385 | — |
| M200000800 | Ccng1 | NM_009831 | AB005559 | CYCLIN G1 (CYCLIN G). |
| M200016031 | Polk | NM_012048 | AB040764 | POLYMERASE (DNA DIRECTED), KAPPA; DINB HOMOLOG 1 (*E. COLI*); DNA DAMAGE-INDUCIBLE PROETIN B; DNA DAMAGE-INDUCIBLE PROTEIN B; POLYMERASE (DNA DIRECTED) KAPPA. |
| M200007794 | Wig1 | NM_009517 | AF012923 | WILD-TYPE P53-INDUCED GENE 1. |
| M300006854 | Sec8 | NM_009148 | BC034644 | EXOCYST COMPLEX COMPONENT SEC8. [Source: SWISSPROT; Acc: O35382] |
| M200006137 | Stinp | NM_021897 | AY034612 | STRESS INDUCED PROTEIN; THYMUS EXPRESSED ACIDIC PROTEIN. |
| M200007477 | 2310047O13Rik | NM_024185 | BC027202 | — |
| M300020474 | — | — | — | — |
| M200003982 | Golga5 | NM_013747 | AF026274 | GOLGI AUTOANTIGEN, GOLGIN SUBFAMILY A, 5. |
| M300020472 | — | — | — | — |

TABLE 1-continued

Genes that distinguish radiation responses in male and female C57B16 mice. Operon Oligo ID can be queried in the OMAD database (http://omad.operon.com)

| Operon OligoID | Gene Symbol | RefSeq | Genbank | Description |
| --- | --- | --- | --- | --- |
| M200004045 | AI504353 | NM_153419 | BC008121 | GLUTAMATE RICH WD REPEAT PROTEIN GRWD.] |
| M200002527 | Cnbp | NM_013493 | U20326 | CELLULAR NUCLEIC ACID BINDING PROTEIN (CNBP).] |
| M200014192 | — | NM_053193 | AF322193 | CLEAVAGE AND POLYADENYLATION SPECIFICITY FACTOR, 160 KDA SUBUNIT (CPSF 160 KDA SUBUNIT).] |
| M300000277 | 2310004L02Rik | NM_025504 | AK009150 | — |
| M200012890 | Smarca4 | — | BC026672 | — |
| M200005377 | Itpr3 | NM_080553 | Z71174 | INOSITOL 1,4,5-TRISPHOSPHATE RECEPTOR TYPE 3 (TYPE 3 INOSITOL 1,4,5-TRISPHOSPHATE RECEPTOR) (TYPE 3 INSP3 RECEPTOR) (IP3 RECEPTOR ISOFORM 3) (INSP3R3) (FRAGMENT). [ |
| M200002473 | Acas2l | NM_080575 | AK088244 | ACETYL-COA SYNTHETASE 2-LIKE; ACETYL-COENZYME A SYNTHETASE 2. |
| M300011684 | Pold1 | NM_011131 | AF024570 | DNA POLYMERASE DELTA CATALYTIC SUBUNIT (EC 2.7.7.7). |
| M300009152 | Tpst1 | NM_013837 | AF038008 | PROTEIN-TYROSINE SULFOTRANSFERASE 1 (EC 2.8.2.20) (TYROSYLPROTEIN SULFOTRANSFERASE-1) (TPST-1). |
| M200014327 | Bcar3 | NM_013867 | BC023930 | BREAST CANCER ANTI-ESTROGEN RESISTANCE3 |
| M300013112 | — | — | J00595 | IG LAMBDA-2 CHAIN C REGION. |
| M200006566 | Gga2 | — | AK004632 | — |
| M300007254 | — | NM_172900 | — | — |
| M200009317 | Scd1 | NM_009127 | BC007474 | ACYL-COA DESATURASE 1 (EC 1.14.19.1) (STEAROYL-COA DESATURASE 1) (FATTY ACID DESATURASE 1) (DELTA(9)-DESATURASE 1). |
| M200001144 | Cd79b | NM_008339 | AF002279 | B-CELL ANTIGEN RECEPTOR COMPLEX ASSOCIATED PROTEIN BETA-CHAIN PRECURSOR (B-CELL-SPECIFIC GLYCOPROTEIN B29) (IMMUNOGLOBULIN-ASSOCIATED B29 PROTEIN) (IG-BETA) (CD79B). |
| M200004687 | Dda3-pending | NM_019976 | AK041835 | DIFFERENTIAL DISPLAY AND ACTIVATED BY P53; P53-REGULATED DDA3. |
| M300020088 | — | — | — | — |
| M300004256 | Fth | NM_010239 | M24509 | FERRITIN HEAVY CHAIN (FERRITIN H SUBUNIT). |
| M300014099 | Actl | NM_013798 | AF195094 | ACTIN-LIKE. |
| M300020371 | — | — | — | — |
| M200006851 | — | NM_026467 | — | RIBOSOMAL PROTEIN S27-LIKE. |
| M300015889 | — | — | — | — |
| M300019801 | — | — | — | — |
| M300018553 | — | — | — | — |
| M300021441 | — | — | — | — |
| M300015305 | — | — | — | — |
| M300019335 | Gapd | NM_008084 | AK002273 | GLYCERALDEHYDE 3-PHOSPHATE DEHYDROGENASE (EC 1.2.1.12) (GAPDH). |
| M300020777 | — | — | — | — |
| M200003258 | Cox8a | NM_007750 | U37721 | CYTOCHROME C OXIDASE POLYPEPTIDE VIII-LIVER, MITOCHONDRIAL PRECURSOR (EC 1.9.3.1). |
| M300014515 | — | — | — | — |
| M300018314 | — | — | — | — |
| M200001083 | Hspa9a | NM_010481 | AK002634 | STRESS-70 PROTEIN, MITOCHONDRIAL PRECURSOR (75 KDA GLUCOSE REGULATED PROTEIN) (GRP 75) (PEPTIDE-BINDING PROTEIN 74) (PBP74) (P66 MOT) (MORTALIN). |
| M300018559 | — | — | — | — |
| M300012796 | Hmgn1 | NM_008251 | X53476 | NONHISTONE CHROMOSOMAL PROTEIN HMG-14 (HIGH-MOBILITY GROUP NUCLEOSOME BINDING DOMAIN 1). |
| M200000777 | G3bp-pending | NM_013716 | AB001927 | RAS-GTPASE-ACTIVATING PROTEIN BINDING PROTEIN 1 (GAP SH3-DOMAIN BINDING PROTEIN 1) (G3BP-1). |
| M300021668 | — | — | — | — |
| M300002115 | Xpo1 | NM_134014 | BC025628 | EXPORTIN 1, CRM1 HOMOLOG; EXPRESSED SEQUENCE AA420417. |
| M300017554 | 4930415K17Rik | NM_133687 | BC016207 | — |
| M300004265 | Ms4a1 | NM_007641 | AK017903 | B-CELL SURFACE PROTEIN CD20 HOMOLOG (B-CELL DIFFERENTIATION ANTIGEN LY-44). |

TABLE 1-continued

Genes that distinguish radiation responses in male and female C57B16 mice. Operon Oligo ID can be queried in the OMAD database (http://omad.operon.com)

| Operon OligoID | Gene Symbol | RefSeq | Genbank | Description |
|---|---|---|---|---|
| M200001144 | Cd79b | NM_008339 | AF002279 | B-CELL ANTIGEN RECEPTOR COMPLEX ASSOCIATED PROTEIN BETA-CHAIN PRECURSOR (B-CELL-SPECIFIC GLYCOPROTEIN B29) (IMMUNOGLOBULIN-ASSOCIATED B29 PROTEIN) (IG-BETA) (CD79B). |
| 1000 Gy | | | | |
| M200007547 | Phlda3 | NM_013750 | BC023408 | PLECKSTRIN HOMOLOGY-LIKE DOMAIN, FAMILY A, MEMBER 3; TDAG/LPL HOMOLOG 1. |
| M200016031 | Polk | NM_012048 | AB040764 | POLYMERASE (DNA DIRECTED), KAPPA; DINB HOMOLOG 1 (E. COLI); DNA DAMAGE-INDUCIBLE PROETIN B; DNA DAMAGE-INDUCIBLE PROTEIN B; POLYMERASE (DNA DIRECTED) KAPPA. |
| M200004687 | Dda3-pending | NM_019976 | AK041835 | DIFFERENTIAL DISPLAY AND ACTIVATED BY P53; P53-REGULATED DDA3. |
| M200007578 | Cdkn1a | NM_007669 | U24173 | CYCLIN-DEPENDENT KINASE INHIBITOR 1 (P21) (CDK-INTERACTING PROTEIN 1) (MELANOMA DIFFERENTIATION ASSOCIATED PROTEIN). |
| M200007794 | Wig1 | NM_009517 | AF012923 | WILD-TYPE P53-INDUCED GENE 1. |
| M200015712 | 3300002K07Rik | NM_152809 | BC033601 | — |
| M300000277 | 2310004L02Rik | NM_025504 | AK009150 | — |
| M300003012 | — | — | — | — |
| M200009576 | Recc1 | NM_011258 | U15037 | ACTIVATOR 1 140 KDA SUBUNIT (REPLICATION FACTOR C LARGE SUBUNIT) (A1 140 KDA SUBUNIT) (RF-C 140 KDA SUBUNIT) (ACTIVATOR 1 LARGE SUBUNIT) (A1-P145) (DIFFERENTIATION SPECIFIC ELEMENT BINDING PROTEIN) (ISRE-BINDING PROTEIN). |
| M300011684 | Pold1 | NM_011131 | AF024570 | DNA POLYMERASE DELTA CATALYTIC SUBUNIT (EC 2.7.7.7). |
| M300010073 | — | — | — | — |
| M200004560 | — | NM_026942 | — | — |
| M200005905 | — | — | BC022623 | — |
| M200002473 | Acas2l | NM_080575 | AK088244 | ACETYL-COA SYNTHETASE 2-LIKE; ACETYL-COENZYME A SYNTHETASE 2. |
| M200006174 | 0610039P13Rik | NM_028752 | BC021548 | — |
| M200014932 | Swap70 | NM_009302 | AF053974 | SWAP COMPLEX PROTEIN; SWAP COMPLEX PROTEIN, 70 KDA. |
| M200006566 | Gga2 | — | AK004632 | — |
| M200000662 | Dtx1 | NM_008052 | AB015422 | DELTEX 1 HOMOLOG (DROSOPHILA); FRACTIONATED X-IRRADIATION INDUCED TRANSCRIPT 1. |
| M300007360 | — | — | — | — |
| M300013112 | — | — | J00595 | IG LAMBDA-2 CHAIN C REGION. |
| M300004265 | Ms4a1 | NM_007641 | AK017903 | B-CELL SURFACE PROTEIN CD20 HOMOLOG (B-CELL DIFFERENTIATION ANTIGEN LY-44). |
| M300007254 | — | NM_172900 | — | — |
| M300000491 | — | — | AF287275 | IG LAMBDA-1 CHAIN V REGION PRECURSOR. |
| M200009317 | Scd1 | NM_009127 | BC007474 | ACYL-COA DESATURASE 1 (EC 1.14.19.1) (STEAROYL-COA DESATURASE 1) (FATTY ACID DESATURASE 1) (DELTA(9)-DESATURASE 1). |
| M200001144 | Cd79b | NM_008339 | AF002279 | B-CELL ANTIGEN RECEPTOR COMPLEX ASSOCIATED PROTEIN BETA-CHAIN PRECURSOR (B-CELL-SPECIFIC GLYCOPROTEIN B29) (IMMUNOGLOBULIN-ASSOCIATED B29 PROTEIN) (IG-BETA) (CD79B). |
| FEMALES | | | | |
| 50 Gy | | | | |
| M300002291 | — | — | — | — |
| M200004687 | Dda3-pending | NM_019976 | AK041835 | DIFFERENTIAL DISPLAY AND ACTIVATED BY P53; P53-REGULATED DDA3. |
| M200000800 | Ccng1 | NM_009831 | AB005559 | CYCLIN G1 (CYCLIN G) |
| M300016629 | — | — | — | — |
| M300020491 | — | — | U38498 | GUANINE NUCLEOTIDE-BINDING PROTEIN G(I)/G(S)/G(O) GAMMA-5 SUBUNIT. |
| M300015969 | — | — | — | — |

TABLE 1-continued

Genes that distinguish radiation responses in male and female C57B16 mice. Operon Oligo ID can be queried in the OMAD database (http://omad.operon.com)

| Operon OligoID | Gene Symbol | RefSeq | Genbank | Description |
| --- | --- | --- | --- | --- |
| M200006491 | Pgls | NM_025396 | BC006594 | 6-PHOSPHOGLUCONOLACTONASE. |
| M300010063 | — | — | — | — |
| M300016018 | — | NM_023133 | — | RIBOSOMAL PROTEIN S19. |
| M200002378 | S100a13 | NM_009113 | BC005687 | S100 CALCIUM-BINDING PROTEIN A13. |
| M300019659 | — | — | — | — |
| M300019012 | — | — | — | — |
| M300009287 | — | — | — | — |
| M300002125 | — | — | — | — |
| M300008077 | Ei24 | NM_007915 | U41751 | ETOPOSIDE-INDUCED PROTEIN 2.4. |
| M200006774 | 2400001E08Rik | NM_025605 | BC020142 | — |
| M300008474 | D10Jhu81e | NM_138601 | AB041855 | — |
| M200000096 | B3Gat3 | NM_024256 | BC002103 | GALACTOSYLGALACTOSYLXYLOSYLPROTEIN 3-BETA-GLUCURONOSYLTRANSFERASE 3 (EC 2.4.1.135) (BETA-1,3-GLUCURONYLTRANSFERASE 3) (GLUCURONOSYLTRANSFERASE-I) (GLCAT-I) (UDP-GLCUA:GAL BETA-1,3-GAL-R GLUCURONYLTRANSFERASE) (GLCUAT-I). |
| M300000948 | — | — | AA277150 | CLATHRIN COAT ASSEMBLY PROTEIN AP17 (CLATHRIN COAT ASSOCIATED PROTEIN AP17) (PLASMA MEMBRANE ADAPTOR AP-2 17 KDA PROTEIN) (HA2 17 KDA SUBUNIT) (CLATHRIN ASSEMBLY PROTEIN 2 SMALL CHAIN). |
| M300001725 | — | NM_175015 | AA275923 | ATP SYNTHASE LIPID-BINDING PROTEIN, MITOCHONDRIAL PRECURSOR (EC 3.6.3.14) (ATP SYNTHASE PROTEOLIPID P3) (ATPASE PROTEIN 9) (ATPASE SUBUNIT C). |
| M300006374 | Psmc2 | — | BC005462 | 26S PROTEASE REGULATORY SUBUNIT 7 (MSS1 PROTEIN). |
| M300005124 | 5730454B08Rik | NM_144530 | BC005786 | — |
| M200000777 | G3bp-pending | NM_013716 | AB001927 | RAS-GTPASE-ACTIVATING PROTEIN BINDING PROTEIN 1 (GAP SH3-DOMAIN BINDING PROTEIN 1) (G3BP-1). |
| M200003749 | — | — | — | — |
| M300018559 | — | — | — | — |
| 200 Gy | | | | |
| M200004687 | Dda3-pending | NM_019976 | AK041835 | DIFFERENTIAL DISPLAY AND ACTIVATED BY P53; P53-REGULATED DDA3. |
| M300020088 | — | — | — | — |
| M300004256 | Fth | NM_010239 | M24509 | FERRITIN HEAVY CHAIN (FERRITIN H SUBUNIT). |
| M300014099 | Actl | NM_013798 | AF195094 | ACTIN-LIKE. |
| M300020371 | — | — | — | — |
| M200006851 | — | NM_026467 | — | RIBOSOMAL PROTEIN S27-LIKE. |
| M300015889 | — | — | — | — |
| M300019801 | — | — | — | — |
| M300018553 | — | — | — | — |
| M300021441 | — | — | — | — |
| M300015305 | — | — | — | — |
| M300019335 | Gapd | NM_008084 | AK002273 | GLYCERALDEHYDE 3-PHOSPHATE DEHYDROGENASE (EC 1.2.1.12) (GAPDH). |
| M300020777 | — | — | — | — |
| M200003258 | Cox8a | NM_007750 | U37721 | CYTOCHROME C OXIDASE POLYPEPTIDE VIII-LIVER, MITOCHONDRIAL PRECURSOR (EC 1.9.3.1). |
| M300014515 | — | — | — | — |
| M300018314 | — | — | — | — |
| M200001083 | Hspa9a | NM_010481 | AK002634 | STRESS-70 PROTEIN, MITOCHONDRIAL PRECURSOR (75 KDA GLUCOSE REGULATED PROTEIN) (GRP 75) (PEPTIDE-BINDING PROTEIN 74) (PBP74) (P66 MOT) (MORTALIN). |
| M300018559 | — | — | — | — |
| M300012796 | Hmgn1 | NM_008251 | X53476 | NONHISTONE CHROMOSOMAL PROTEIN HMG-14 (HIGH-MOBILITY GROUP NUCLEOSOME BINDING DOMAIN 1). |
| M200000777 | G3bp-pending | NM_013716 | AB001927 | RAS-GTPASE-ACTIVATING PROTEIN BINDING PROTEIN 1 (GAP SH3-DOMAIN BINDING PROTEIN 1) (G3BP-1). |
| M300021668 | — | — | — | — |
| M300002115 | Xpo1 | NM_134014 | BC025628 | EXPORTIN 1, CRM1 HOMOLOG; EXPRESSED SEQUENCE AA420417. |
| M300017554 | 4930415K17Rik | NM_133687 | BC016207 | — |

TABLE 1-continued

Genes that distinguish radiation responses in male and female C57Bl6 mice. Operon Oligo ID can be queried in the OMAD database (http://omad.operon.com)

| Operon OligoID | Gene Symbol | RefSeq | Genbank | Description |
|---|---|---|---|---|
| M300004265 | Ms4a1 | NM_007641 | AK017903 | B-CELL SURFACE PROTEIN CD20 HOMOLOG (B-CELL DIFFERENTIATION ANTIGEN LY-44). |
| M200001144 | Cd79b | NM_008339 | AF002279 | B-CELL ANTIGEN RECEPTOR COMPLEX ASSOCIATED PROTEIN BETA-CHAIN PRECURSOR (B-CELL-SPECIFIC GLYCOPROTEIN B29) (IMMUNOGLOBULIN-ASSOCIATED B29 PROTEIN) (IG-BETA) (CD79B). |
| 1000 Gy | | | | |
| M200004687 | Dda3-pending | NM_019976 | AK041835 | DIFFERENTIAL DISPLAY AND ACTIVATED BY P53; P53-REGULATED DDA3. |
| M300008077 | Ei24 | NM_007915 | U41751 | ETOPOSIDE-INDUCED PROTEIN 2.4. |
| M300011848 | — | NM_173445 | — | — |
| M300020371 | — | — | — | — |
| M300019400 | — | — | — | — |
| M300019801 | — | — | — | — |
| M300014889 | Gapd | NM_008084 | AK002273 | GLYCERALDEHYDE 3-PHOSPHATE DEHYDROGENASE (EC 1.2.1.12) (GAPDH). |
| M300019335 | Gapd | NM_008084 | AK002273 | GLYCERALDEHYDE 3-PHOSPHATE DEHYDROGENASE (EC 1.2.1.12) (GAPDH). |
| M300000465 | 2610301D06Rik | NM_026007 | AK014277 | ELONGATION FACTOR 1-GAMMA (EF-1-GAMMA) (EEF-1B GAMMA). |
| M300019589 | — | — | — | — |
| M300012879 | — | — | AK007389 | SMALL NUCLEAR RIBONUCLEOPROTEIN SM D2 (SNRNP CORE PROTEIN D2) (SM-D2). |
| M300002970 | 5730420B22Rik | NM_172597 | AK017582 | — |
| M300021668 | — | — | — | — |
| M300011495 | — | — | BG088667 | SESTRIN 1 (P53-REGULATED PROTEIN PA26). |
| M300017752 | — | — | AF516285 | ANTI-VIPASE LIGHT CHAIN VARIABLE REGION (FRAGMENT). |
| M300007254 | — | NM_172900 | — | — |
| M200006566 | Gga2 | — | AK004632 | — |
| M200006174 | 0610039P13Rik | NM_028752 | BC021548 | — |
| M200000312 | Ly6d | NM_010742 | L40419 | LYMPHOCYTE ANTIGEN LY-6D PRECURSOR (THYMOCYTE B CELL ANTIGEN) (THB). |
| M200000320 | Pou2af1 | NM_011136 | U43788 | POU DOMAIN CLASS 2, ASSOCIATING FACTOR 1 (B-CELL-SPECIFIC COACTIVATOR OBF-1) (OCT BINDING FACTOR 1) (BOB-1) (BOB1) (OCA-B). |
| M200001703 | Cd19 | NM_009844 | M84372 | B-LYMPHOCYTE ANTIGEN CD19 PRECURSOR (B-LYMPHOCYTE SURFACE ANTIGEN B4) (LEU-12) (DIFFERENTIATION ANTIGEN CD19). |
| M200000715 | BB219290 | NM_145141 | AF426462 | FC RECEPTOR HOMOLOG EXPRESSED IN B CELLS; FC RECEPTOR RELATED PROTEIN X. |
| M200002822 | Blnk | NM_008528 | AJ298054 | B-CELL LINKER; LYMPHOCYTE ANTIGEN 57. |
| M200001144 | Cd79b | NM_008339 | AF002279 | B-CELL ANTIGEN RECEPTOR COMPLEX ASSOCIATED PROTEIN BETA-CHAIN PRECURSOR (B-CELL-SPECIFIC GLYCOPROTEIN B29) (IMMUNOGLOBULIN-ASSOCIATED B29 PROTEIN) (IG-BETA) (CD79B). |
| M200009317 | Scd1 | NM_009127 | BC007474 | ACYL-COA DESATURASE 1 (EC 1.14.19.1) (STEAROYL-COA DESATURASE 1) (FATTY ACID DESATURASE 1) (DELTA(9)-DESATURASE 1). |

TABLE 2

Genes that overlap between mouse groups. Operon Oligo ID can be queried in the OMAD database (http://omad.operon.com)

| Operon OligoID | Gene Symbol | RefSeq | Genbank | Description |
|---|---|---|---|---|
| SEX | | | | |
| C57Bl6 M and C57Bl6 F | | | | |
| M vs F 50cGy | | | | |
| M200000800 | Ccng1 | NM_009831 | AB005559 | CYCLIN G1 (CYCLIN G) |
| M200004687 | Dda3 | NM_019976 | AK041835 | DIFFERENTIAL DISPLAY AND ACTIVATED BY P53; P53-REGULATED DDA3. |

TABLE 2-continued

Genes that overlap between mouse groups. Operon Oligo ID can be queried in the OMAD database (http://omad.operon.com)

| Operon OligoID | Gene Symbol | RefSeq | Genbank | Description |
|---|---|---|---|---|
| M vs F 200cGy | | | | |
| M200001144 | Cd79b | NM_008339 | AF002279 | B-CELL ANTIGEN RECEPTOR COMPLEX ASSOCIATED PROTEIN BETA-CHAIN PRECURSOR (B-CELL-SPECIFIC GLYCOPROTEIN B29) (IMMUNOGLOBULIN-ASSOCIATED B29 PROTEIN) (IG-BETA) (CD79B). |
| M vs F 1000cGy | | | | |
| M200001144 | Cd79b | NM_008339 | AF002279 | B-CELL ANTIGEN RECEPTOR COMPLEX ASSOCIATED PROTEIN BETA-CHAIN PRECURSOR (B-CELL-SPECIFIC GLYCOPROTEIN B29) (IMMUNOGLOBULIN-ASSOCIATED B29 PROTEIN) (IG-BETA) (CD79B). |
| M200004687 | Dda3 | NM_019976 | AK041835 | DIFFERENTIAL DISPLAY AND ACTIVATED BY P53; P53-REGULATED DDA3. |
| M200009317 | Scd1 | NM_009127 | BC007474 | ACYL-COA DESATURASE 1 (EC 1.14.19.1) (STEAROYL-COA DESATURASE 1) (FATTY ACID DESATURASE 1) (DELTA(9)-DESATURASE 1). |
| M200006566 M200006174 M300007254 | Gga2 | — | AK004632 | — |
| GENOTYPE | | | | |
| C57Bl6 F and BALB/c F | | | | |
| Bl vs BA 50cGy | | | | |
| M200000800 | Ccng1 | NM_009831 | AB005559 | CYCLIN G1 (CYCLIN G) |
| M200004687 | Dda3 | NM_019976 | AK041835 | DIFFERENTIAL DISPLAY AND ACTIVATED BY P53; P53-REGULATED DDA3. |
| M300008077 | Ei24 | NM_007915 | U41751 | ETOPOSIDE-INDUCED PROTEIN 2.4. |
| Bl vs BA 200cGy | | | | |
| M200004687 | Dda3 | NM_019976 | AK041835 | DIFFERENTIAL DISPLAY AND ACTIVATED BY P53; P53-REGULATED DDA3. |
| Bl vs BA 1000cGy | | | | |
| M200004687 | Dda3 | NM_019976 | AK041835 | DIFFERENTIAL DISPLAY AND ACTIVATED BY P53; P53-REGULATED DDA3. |
| TIME | | | | |
| Within C57Bl6 F | | | | |
| 6 hr vs 24 hr 50cGy | | | | |
| None | | | | |
| 6 hr vs 24 hr 200cGy | | | | |
| None | | | | |
| 6 hr vs 24 hr 1000cGy | | | | |
| None | | | | |
| 6 hr vs 7 d 50cGy | | | | |
| None | | | | |
| 6 hr vs 7 d 200cGy | | | | |
| None | | | | |
| 24 h vs 7 d 50cGy | | | | |
| M300000165 | Lgals1 | NM_008495 | AK004298 | GALECTIN-1 (BETA-GALACTOSIDE-BINDING LECTIN L-14-I) (LACTOSE-BINDING LECTIN 1) (S-LAC LECTIN 1) |
| 24 h vs 7 d 200cGy | | | | |
| None | | | | |

Impact of Genotype on Prediction of Radiation Status

Figure 3A:
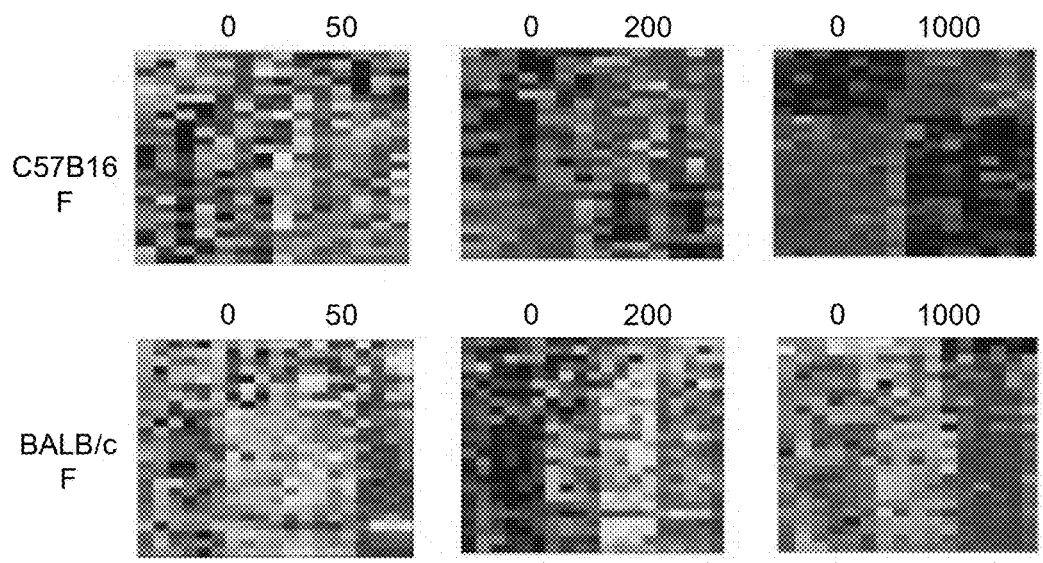
FIGS. 3A-3C. Impact of genotype on murine irradiation profiles.
Figure 3B:
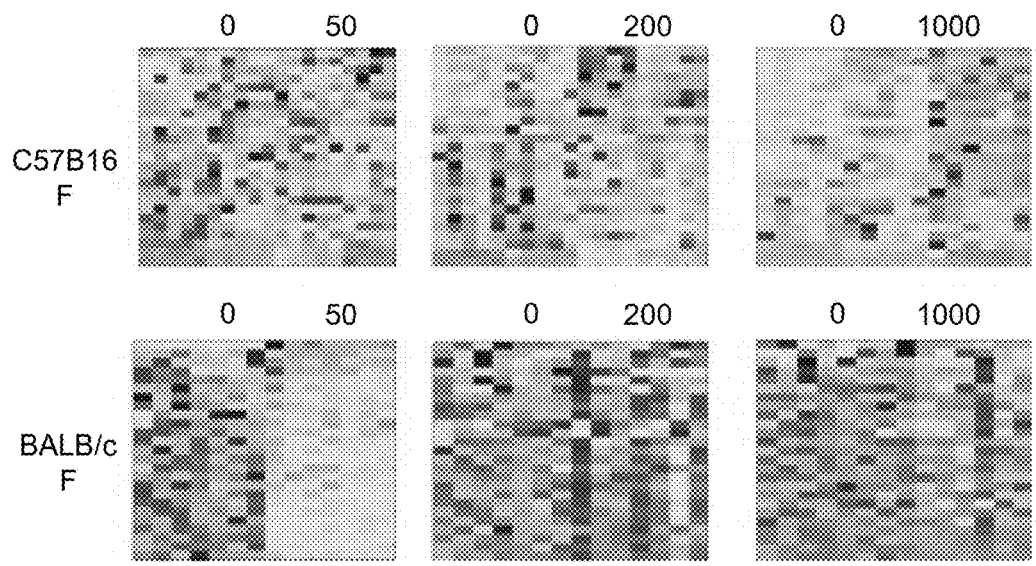
Figure 3C:
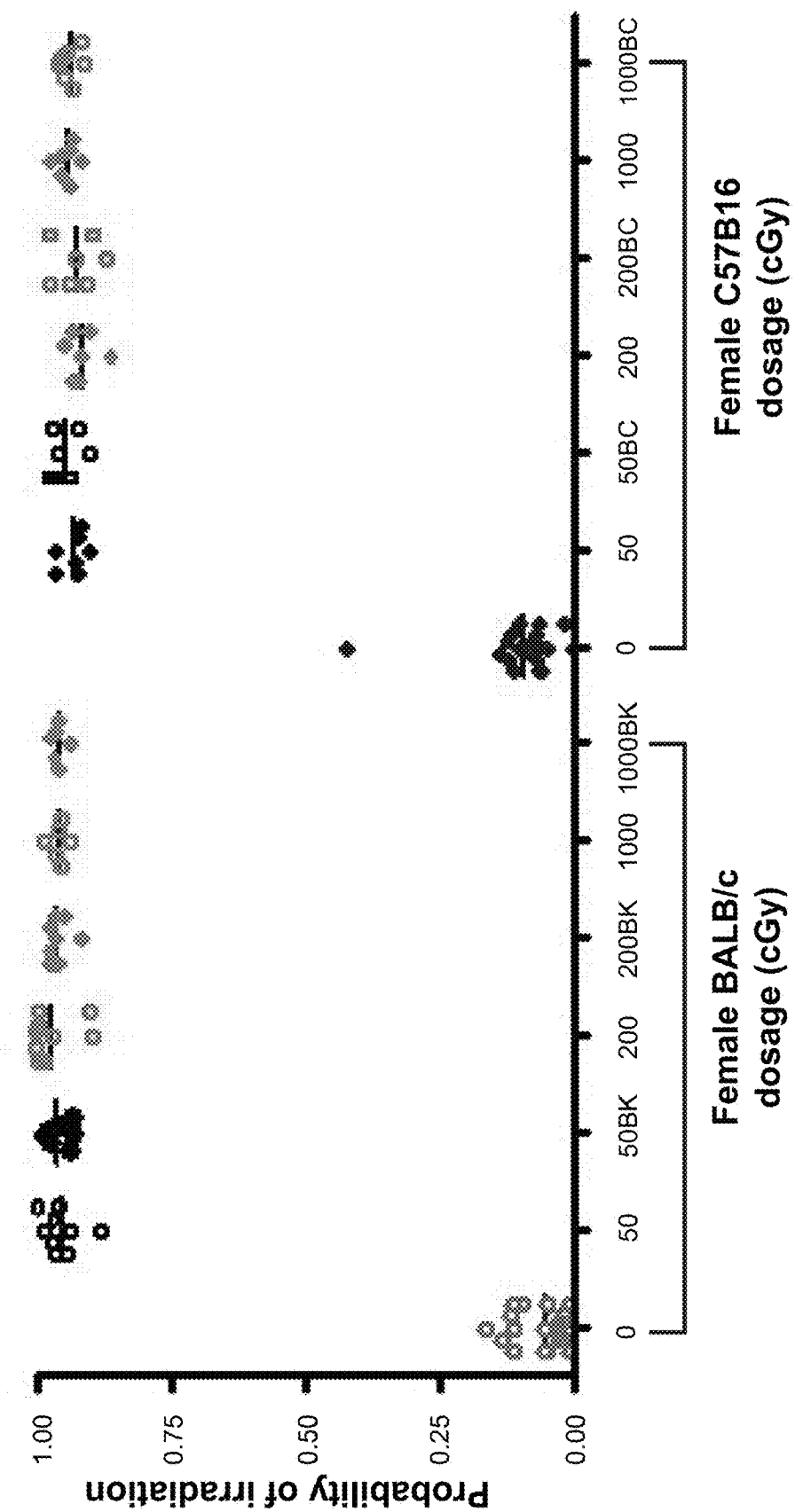

Since the human population is genetically diverse, an examination was next made to determine whether gene expression signatures of radiation exposure could accurately predict the status of mice across different genotypes. PB was collected from C57Bl6 and BALB/c mice at 6 hours following 50 cGy, 200 cGy or 1000 cGy. It was possible to identify patterns of gene expression which appeared to distinguish the different levels of radiation from the non-irradiated controls within each strain (FIG. 3A). However, when the PB gene expression signatures from C57Bl6 mice were tested against BALB/c mice, and vice versa, the gene expression profiles were less distinct (FIG. 3B). A leave-one-out cross-validation analysis was then performed in which gene expression profiles from C57Bl6 mice were tested against PB from BALB/c mice and found that the metagene predictors of radiation from C57Bl6 mice displayed 100% accuracy in predicting the status of non-irradiated and irradiated BALB/c mice (FIG. 3C). Similarly, application of the PB metagene profiles of radiation generated in BALB/c mice demonstrated 100% accuracy in distinguishing non-irradiated and irradiated C57Bl6 mice. Interestingly, less than 20% of the genes represented within the PB predictors from C57Bl6 mice and BALB/c mice overlapped (Table 3, Table 2), but both predictors were highly accurate in predicting the radiation status of the different strain of mice. Dda3, a p53-inducible gene, which participates in suppression of cell growth (Hsieh et al, Oncogene 21:3050-3057 (2002)), was represented in both strains at all radiation doses.

TABLE 3

Genes that distinguish radiation responses in BALB/c mice. Operon Oligo ID can be queried in the OMAD database (http://omad.operon.com)

| Operon OligoID | Gene Symbol | RefSeq | Genbank | Description |
|---|---|---|---|---|
| 50 Gy | | | | |
| M200013484 | 9030617O03Rik | NM_145448 | BC021385 | — |
| M200004687 | Dda3-pending | NM_019976 | AK041835 | DIFFERENTIAL DISPLAY AND ACTIVATED BY P53; P53-REGULATED DDA3. |
| M300000487 | Bax | NM_007527 | L22472 | APOPTOSIS REGULATOR BAX, MEMBRANE ISOFORM ALPHA. |
| M300006855 | SecB | NM_009148 | BC034644 | EXOCYST COMPLEX COMPONENT SEC8. |
| M300001199 | — | — | BC002257 | — |
| M200000800 | Ccng1 | NM_009831 | AB005559 | CYCLIN G1 (CYCLIN G). |
| M200016031 | Polk | NM_012048 | AB040764 | POLYMERASE (DNA DIRECTED), KAPPA; DINB HOMOLOG 1 (E. COLI); DNA DAMAGE-INDUCIBLE PROETIN B; DNA DAMAGE-INDUCIBLE PROTEIN B; POLYMERASE (DNA DIRECTED) KAPPA. |
| M200003784 | Bax | NM_007527 | L22472 | APOPTOSIS REGULATOR BAX, MEMBRANE ISOFORM ALPHA. |
| M200007547 | Phlda3 | NM_013750 | BC023408 | PLECKSTRIN HOMOLOGY-LIKE DOMAIN, FAMILY A, MEMBER 3; TDAG/LPL HOMOLOG 1. |
| M300010491 | D030041N15Rik | NM_153416 | BC018191 | ALADIN (ADRACALIN). |
| M200006364 | Dcxr | NM_026428 | AK004023 | DIACETYL/L-XYLULOSE REDUCTASE. |
| M300007324 | 2700083B06Rik | NM_026531 | BC022614 | — |
| M300000486 | Bax | NM_007527 | L22472 | APOPTOSIS REGULATOR BAX, MEMBRANE ISOFORM ALPHA. |
| M200007794 | Wig1 | NM_009517 | AF012923 | WILD-TYPE P53-INDUCED GENE 1. |
| M300008077 | Ei24 | NM_007915 | U41751 | ETOPOSIDE-INDUCED PROTEIN 2.4. |
| M300003395 | Ly6e | NM_008529 | U47737 | LYMPHOCYTE ANTIGEN LY-6E PRECURSOR (THYMIC SHARED ANTIGEN-1) (TSA-1) (STEM CELL ANTIGEN 2). |
| M200003474 | D730042P09Rik | NM_144543 | AB080370 | THYMOCYTE PROTEIN THY28. |
| M200012250 | Scd2 | NM_009128 | M26270 | ACYL-COA DESATURASE 2 (EC 1.14.19.1) (STEAROYL-COA DESATURASE 2) (FATTY ACID DESATURASE 2) (DELTA(9)-DESATURASE 2). |
| M200000655 | Tnfrsf6 | NM_007987 | S56486 | TUMOR NECROSIS FACTOR RECEPTOR SUPERFAMILY MEMBER 6 PRECURSOR (FASL RECEPTOR) (APOPTOSIS-MEDIATING SURFACE ANTIGEN FAS) (APO-1 ANTIGEN) (CD95). |
| M200008006 | 2410089B13Rik | — | AK010745 | — |
| M200000279 | Ly6e | NM_008529 | U47737 | LYMPHOCYTE ANTIGEN LY-6E PRECURSOR (THYMIC SHARED ANTIGEN-1) (TSA-1) (STEM CELL ANTIGEN 2). |
| M200000354 | ORF21 | NM_145482 | BC029101 | — |
| M300002140 | D11Ertd603e | NM_026023 | AK004388 | — |
| M300002232 | Ppm1d | NM_016910 | AF200464 | PROTEIN PHOSPHATASE 2C DELTA ISOFORM (EC 3.1.3.16) (PP2C-DELTA) (P53-INDUCED PROTEIN PHOSPHATASE 1) (PROTEIN PHOSPHATASE MAGNESIUM-DEPENDENT 1 DELTA). |
| M300002800 | Zfp369 | — | BC036565 | NEUROTROPHIN RECEPTOR INTERACTING FACTOR 2. |
| 200 Gy | | | | |
| M200004687 | Dda3-pending | NM_019976 | AK041835 | DIFFERENTIAL DISPLAY AND ACTIVATED BY P53; P53-REGULATED DDA3. |
| M300020088 | — | — | — | — |
| M300004256 | Fth | NM_010239 | M24509 | FERRITIN HEAVY CHAIN (FERRITIN H SUBUNIT). |
| M300014099 | Actl | NM_013798 | AF195094 | ACTIN-LIKE. |
| M300020371 | — | — | — | — |

TABLE 3-continued

Genes that distinguish radiation responses in BALB/c mice. Operon Oligo ID can be queried in the OMAD database (http://omad.operon.com)

| Operon OligoID | Gene Symbol | RefSeq | Genbank | Description |
|---|---|---|---|---|
| M200006851 | — | NM_026467 | — | RIBOSOMAL PROTEIN S27-LIKE. |
| M300015889 | — | — | — | — |
| M300019801 | — | — | — | — |
| M300018553 | — | — | — | — |
| M300021441 | — | — | — | — |
| M300015305 | — | — | — | — |
| M300019335 | Gapd | NM_008084 | AK002273 | GLYCERALDEHYDE 3-PHOSPHATE DEHYDROGENASE (EC 1.2.1.12) (GAPDH). |
| M300020777 | — | — | — | — |
| M200003258 | Cox8a | NM_007750 | U37721 | CYTOCHROME C OXIDASE POLYPEPTIDE VIII-LIVER, MITOCHONDRIAL PRECURSOR (EC 1.9.3.1). |
| M300014515 | — | — | — | — |
| M300018314 | — | — | — | — |
| M200001083 | Hspa9a | NM_010481 | AK002634 | STRESS-70 PROTEIN, MITOCHONDRIAL PRECURSOR (75 KDA GLUCOSE REGULATED PROTEIN) (GRP 75) (PEPTIDE-BINDING PROTEIN 74) (PBP74) (P66 MOT) (MORTALIN). |
| M300018559 | — | — | — | — |
| M300012796 | Hmgn1 | NM_008251 | X53476 | NONHISTONE CHROMOSOMAL PROTEIN HMG-14 (HIGH-MOBILITY GROUP NUCLEOSOME BINDING DOMAIN 1). |
| M200000777 | G3bp-pending | NM_013716 | AB001927 | RAS-GTPASE-ACTIVATING PROTEIN BINDING PROTEIN 1 (GAP SH3-DOMAIN BINDING PROTEIN 1) (G3BP-1). |
| M300021668 | — | — | — | — |
| M300002115 | Xpo1 | NM_134014 | BC025628 | EXPORTIN 1, CRM1 HOMOLOG; EXPRESSED SEQUENCE AA420417. |
| M300017554 | 4930415K17Rik | NM_133687 | BC016207 | — |
| M300004265 | Ms4a1 | NM_007641 | AK017903 | B-CELL SURFACE PROTEIN CD20 HOMOLOG (B-CELL DIFFERENTIATION ANTIGEN LY-44). |
| M200001144 | Cd79b | NM_008339 | AF002279 | B-CELL ANTIGEN RECEPTOR COMPLEX ASSOCIATED PROTEIN BETA-CHAIN PRECURSOR (B-CELL-SPECIFIC GLYCOPROTEIN B29) (IMMUNOGLOBULIN-ASSOCIATED B29 PROTEIN) (IG-BETA) (CD79B). |

1000 Gy

| Operon OligoID | Gene Symbol | RefSeq | Genbank | Description |
|---|---|---|---|---|
| M200004687 | Dda3-pending | NM_019976 | AK041835 | DIFFERENTIAL DISPLAY AND ACTIVATED BY P53; P53-REGULATED DDA3. |
| M300008077 | Ei24 | NM_007915 | U41751 | ETOPOSIDE-INDUCED PROTEIN 2.4. |
| M300011848 | — | NM_173445 | — | — |
| M300020371 | — | — | — | — |
| M300019400 | — | — | — | — |
| M300019801 | — | — | — | — |
| M300014889 | Gapd | NM_008084 | AK002273 | GLYCERALDEHYDE 3-PHOSPHATE DEHYDROGENASE (EC 1.2.1.12) (GAPDH). |
| M300019335 | Gapd | NM_008084 | AK002273 | GLYCERALDEHYDE 3-PHOSPHATE DEHYDROGENASE (EC 1.2.1.12) (GAPDH). |
| M300000465 | 2610301D06Rik | NM_026007 | AK014277 | ELONGATION FACTOR 1-GAMMA (EF-1-GAMMA) (EEF-1B GAMMA). |
| M300019589 | — | — | — | — |
| M300012879 | — | — | AK007389 | SMALL NUCLEAR RIBONUCLEOPROTEIN SM D2 (SNRNP CORE PROTEIN D2) (SM-D2). |
| M300002970 | 5730420B22Rik | NM_172597 | AK017582 | — |
| M300021668 | — | — | — | — |
| M300011495 | — | — | BG088667 | SESTRIN 1 (P53-REGULATED PROTEIN PA26). |
| M300017752 | — | — | AF516285 | ANTI-VIPASE LIGHT CHAIN VARIABLE REGION (FRAGMENT). |
| M300007254 | — | NM_172900 | — | — |
| M200006566 | Gga2 | — | AK004632 | — |
| M200006174 | 0610039P13Rik | NM_028752 | BC021548 | — |
| M200000312 | Ly6d | NM_010742 | L40419 | LYMPHOCYTE ANTIGEN LY-6D PRECURSOR (THYMOCYTE B CELL ANTIGEN) (THB). |
| M200000320 | Pou2af1 | NM_011136 | U43788 | POU DOMAIN CLASS 2, ASSOCIATING FACTOR 1 (B-CELL-SPECIFIC COACTIVATOR OBF-1) (OCT BINDING FACTOR 1) (BOB-1) (BOB1) (OCA-B). |
| M200001703 | Cd19 | NM_009844 | M84372 | B-LYMPHOCYTE ANTIGEN CD19 PRECURSOR (B-LYMPHOCYTE SURFACE ANTIGEN B4) (LEU-12) (DIFFERENTIATION ANTIGEN CD19). |
| M200000715 | BB219290 | NM_145141 | AF426462 | FC RECEPTOR HOMOLOG EXPRESSED IN B CELLS; FC RECEPTOR RELATED PROTEIN X. |

TABLE 3-continued

Genes that distinguish radiation responses in BALB/c mice. Operon Oligo ID can be queried in the OMAD database (http://omad.operon.com)

| Operon OligoID | Gene Symbol | RefSeq | Genbank | Description |
|---|---|---|---|---|
| M200002822 | Blnk | NM_008528 | AJ298054 | B-CELL LINKER; LYMPHOCYTE ANTIGEN 57. |
| M200001144 | Cd79b | NM_008339 | AF002279 | B-CELL ANTIGEN RECEPTOR COMPLEX ASSOCIATED PROTEIN BETA-CHAIN PRECURSOR (B-CELL-SPECIFIC GLYCOPROTEIN B29) (IMMUNOGLOBULIN-ASSOCIATED B29 PROTEIN) (IG-BETA) (CD79B). |
| M200009317 | Scd1 | NM_009127 | BC007474 | ACYL-COA DESATURASE 1 (EC 1.14.19.1) (STEAROYL-COA DESATURASE 1) (FATTY ACID DESATURASE 1) (DELTA(9)-DESATURASE 1). |

The Impact of Time on PB Gene Expression Signatures of Irradiation

Figure 4A:
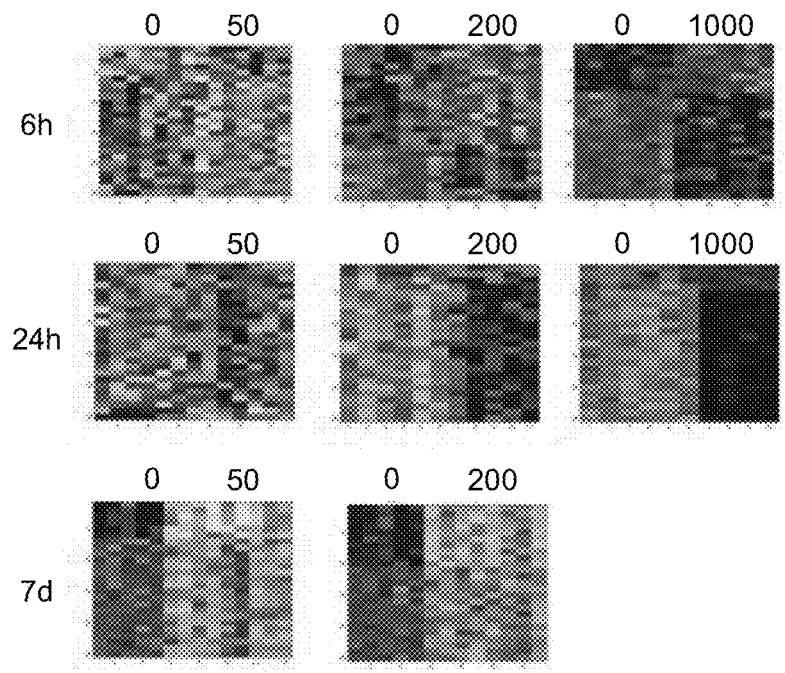
FIGS. 4A-4C. Impact of time on murine irradiation profiles.
Figure 4B:
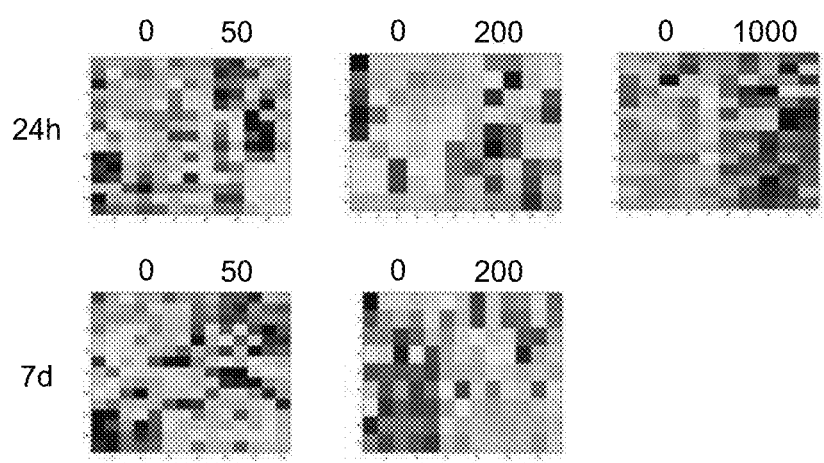
Figure 4C:
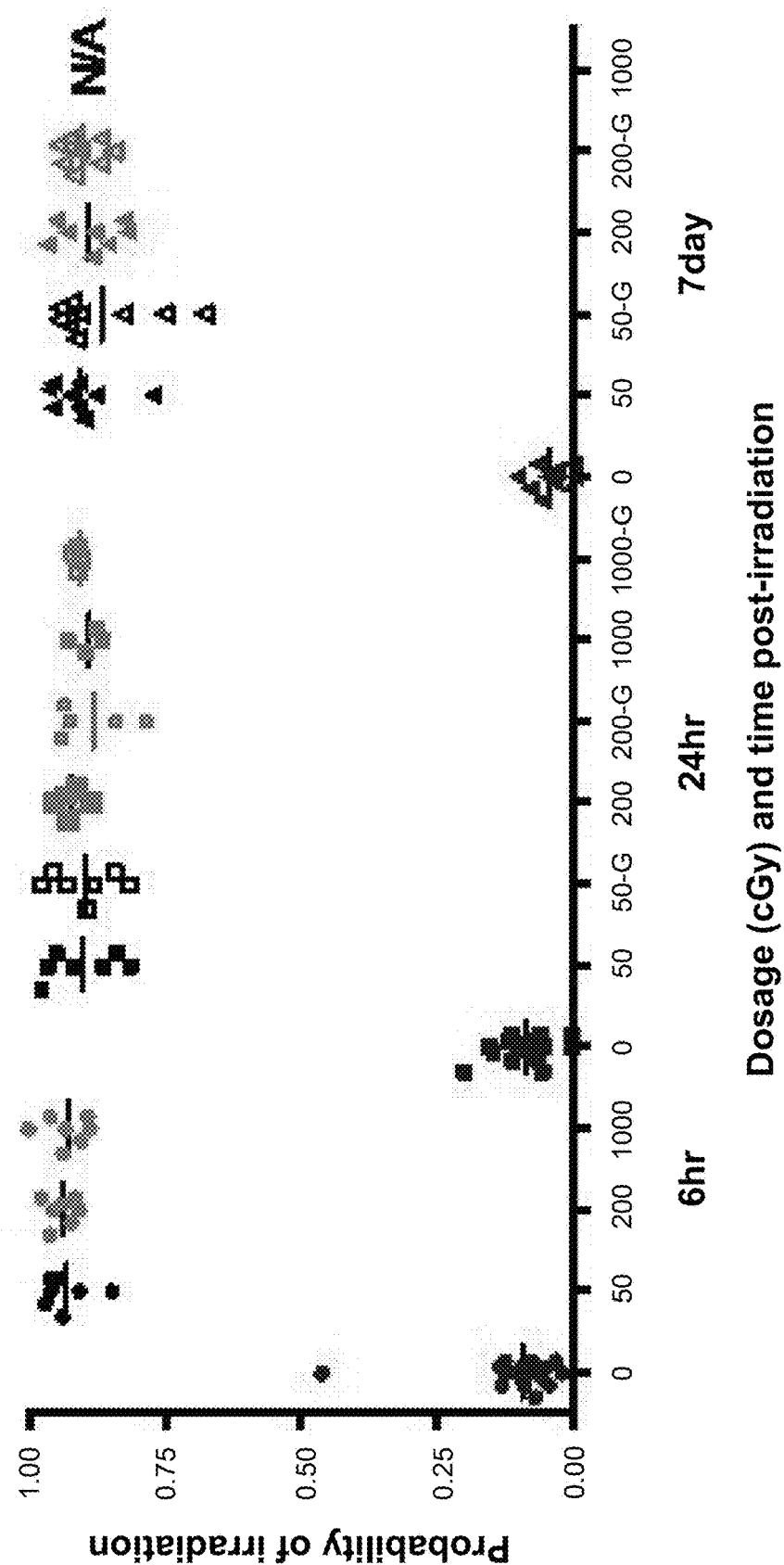

PB responses to environmental exposures may change over time as a function of changes in PB cellular composition and cellular responses themselves. Patterns of gene expression were identified in the PB of C57Bl6 female mice at 6 hrs, 24 hrs and 7 days post-irradiation which appeared to distinguish the 3 different levels of radiation versus non-irradiated mice (FIG. 4A). When the PB metagene profiles of radiation exposure generated from the 6 hr time point were applied against PB samples from mice at the 24 hr and 7 day time points post-irradiation, the profiles appeared less distinct (FIG. 4B). A leave-one-out cross-validation analysis demonstrated that the PB metagene profiles from each time point predicted each dose of radiation with 100% accuracy (FIG. 4C). Next, a leave-one-out cross-validation analysis was performed using the metagene profiles from the 6 hr time point against each of the PB samples from mice at 24 hr and 7 day time points and the 6 hr metagene profiles demonstrated 100% accuracy in predicting the radiation status of the 24 hr and 7 day time point samples (FIG. 4C). Of note, the 7 day time point following 1000 cGy exposure could not be analyzed since it was not possible to collect sufficient RNA from these PB samples to allow gene array hybridization to be performed. Although it was found that time did not impact the accuracy of PB gene expression profiles in predicting radiation status, the lists of genes which comprised these PB signatures changed significantly over 7 days (Table 4). No genes were found in common between the 6 hr predictors and the 24 hr or 7 day PB signatures of radiation in 50 cGy-, 200 cGy-, or 1000 cGy-treated mice (Table 2). A single gene, Galectin 1 (Lgals1), a carbohydrate binding protein that is involved in the induction of cell death (Valenzuela et al, Cancer Res. 67:6155-6162 (2007)), was found in common between the 24 hr and 7 day predictors of 50 cGy.

TABLE 4

Genes that distinguish the impact of time in C57Bl6 mice. Operon Oligo ID can be queried in the OMAD database (http://omad.operon.com)

| Operon Oligo ID | Gene Symbol | RefSeq | Genbank | Description |
|---|---|---|---|---|
| Female C57Bl6 6 hr 50 cGy | | | | |
| M300002291 | — | — | — | — |
| M200004687 | Dda3-pending | NM_019976 | AK041835 | DIFFERENTIAL DISPLAY AND ACTIVATED BY P53; P53-REGULATED DDA3. |
| M200000800 | Ccng1 | NM_009831 | AB005559 | CYCLIN G1 (CYCLIN G). |
| M300016629 | — | — | — | — |
| M300020491 | — | — | U38498 | GUANINE NUCLEOTIDE-BINDING PROTEIN G(I)/G(S)/G(O) GAMMA-5 SUBUNIT. |
| M300015969 | — | — | — | — |
| M300010063 | — | — | — | — |
| M300016018 | — | NM_023133 | — | RIBOSOMAL PROTEIN S19. |
| M200002378 | S100a13 | NM_009113 | BC005687 | S100 CALCIUM-BINDING PROTEIN A13. |
| M300019659 | — | — | — | — |
| M300014141 | V1rc22 | NM_134177 | AY065478 | VOMERONASAL 1 RECEPTOR, C22. |
| M300020488 | — | — | V00754 | HISTONE H3.4 (EMBRYONIC). |
| M300019012 | — | — | — | — |
| M300014338 | — | — | — | — |
| M300009287 | — | — | — | — |
| M300002125 | — | — | — | — |
| M300008077 | Ei24 | NM_007915 | U41751 | ETOPOSIDE-INDUCED PROTEIN 2.4. |
| M200006774 | 2400001E08Rik | NM_025605 | BC020142 | — |
| M300008474 | D10Jhu81e | NM_138601 | AB041855 | — |
| M200000096 | B3Gat3 | NM_024256 | BC002103 | GALACTOSYLGALACTOSYLXYLOSYLPROTEIN 3-BETA-GLUCURONOSYLTRANSFERASE 3 (EC 2.4.1.135) (BETA-1,3-GLUCURONYLTRANSFERASE 3) (GLUCURONOSYLTRANSFERASE-I) (GLCAT-I) |

TABLE 4-continued

Genes that distinguish the impact of time in C57B16 mice. Operon Oligo ID can be queried in the OMAD database (http://omad.operon.com)

| Operon Oligo ID | Gene Symbol | RefSeq | Genbank | Description |
|---|---|---|---|---|
| M300006374 | Psmc2 | — | BC005462 | (UDP-GLCUA:GAL BETA-1,3-GAL-R GLUCURONYLTRANSFERASE) (GLCUAT-I). 26S PROTEASE REGULATORY SUBUNIT 7 (MSS1 PROTEIN). |
| M300005124 | 5730454B08Rik | NM_144530 | BC005786 | — |
| M200000777 | G3bp-pending | NM_013716 | AB001927 | RAS-GTPASE-ACTIVATING PROTEIN BINDING PROTEIN 1 (GAP SH3-DOMAIN BINDING PROTEIN 1) (G3BP-1). |
| M200003749 | — | — | — | — |
| M300018559 | — | — | — | — |
| Female C57Bl6 6 hr 200 cGy | | | | |
| M200004687 | Dda3-pending | NM_019976 | AK041835 | DIFFERENTIAL DISPLAY AND ACTIVATED BY P53; P53-REGULATED DDA3. |
| M300020088 | — | — | — | — |
| M300004256 | Fth | NM_010239 | M24509 | FERRITIN HEAVY CHAIN (FERRITIN H SUBUNIT). |
| M300014099 | Actl | NM_013798 | AF195094 | ACTIN-LIKE. |
| M300020371 | — | — | — | — |
| M200006851 | — | NM_026467 | — | RIBOSOMAL PROTEIN S27-LIKE. |
| M300015889 | — | — | — | — |
| M300019801 | — | — | — | — |
| M300018553 | — | — | — | — |
| M300021441 | — | — | — | — |
| M300015305 | — | — | — | — |
| M300019335 | Gapd | NM_008084 | AK002273 | GLYCERALDEHYDE 3-PHOSPHATE DEHYDROGENASE (EC 1.2.1.12) (GAPDH). |
| M300020777 | — | — | — | — |
| M200003258 | Cox8a | NM_007750 | U37721 | CYTOCHROME C OXIDASE POLYPEPTIDE VIII-LIVER, MITOCHONDRIAL PRECURSOR (EC 1.9.3.1). |
| M300014515 | — | — | — | — |
| M300018314 | — | — | — | — |
| M200001083 | Hspa9a | NM_010481 | AK002634 | STRESS-70 PROTEIN, MITOCHONDRIAL PRECURSOR (75 KDA GLUCOSE REGULATED PROTEIN) (GRP 75) (PEPTIDE-BINDING PROTEIN 74) (PBP74) (P66 MOT) (MORTALIN). |
| M300018559 | — | — | — | — |
| M300012796 | Hmgn1 | NM_008251 | X53476 | NONHISTONE CHROMOSOMAL PROTEIN HMG-14 (HIGH-MOBILITY GROUP NUCLEOSOME BINDING DOMAIN 1). |
| M200000777 | G3bp-pending | NM_013716 | AB001927 | RAS-GTPASE-ACTIVATING PROTEIN BINDING PROTEIN 1 (GAP SH3-DOMAIN BINDING PROTEIN 1) (G3BP-1). |
| M300021668 | — | — | — | — |
| M300002115 | Xpo1 | NM_134014 | BC025628 | EXPORTIN 1, CRM1 HOMOLOG; EXPRESSED SEQUENCE AA420417. |
| M300017554 | 4930415K17Rik | NM_133687 | BC016207 | — |
| M300004265 | Ms4a1 | NM_007641 | AK017903 | B-CELL SURFACE PROTEIN CD20 HOMOLOG (B-CELL DIFFERENTIATION ANTIGEN LY-44). |
| M200001144 | Cd79b | NM_008339 | AF002279 | B-CELL ANTIGEN RECEPTOR COMPLEX ASSOCIATED PROTEIN BETA-CHAIN PRECURSOR (B-CELL-SPECIFIC GLYCOPROTEIN B29) (IMMUNOGLOBULIN-ASSOCIATED B29 PROTEIN) (IG-BETA) (CD79B). |
| Female C57Bl6 6 hr 1000 cGy | | | | |
| M200004687 | Dda3-pending | NM_019976 | AK041835 | DIFFERENTIAL DISPLAY AND ACTIVATED BY P53; P53-REGULATED DDA3. |
| M300008077 | Ei24 | NM_007915 | U41751 | ETOPOSIDE-INDUCED PROTEIN 2.4. |
| M300011848 | — | NM_173445 | — | — |
| M300020371 | — | — | — | — |
| M300019852 | — | — | — | — |
| M300019400 | — | — | — | — |
| M300019801 | — | — | — | — |
| M300014889 | Gapd | NM_008084 | AK002273 | GLYCERALDEHYDE 3-PHOSPHATE DEHYDROGENASE (EC 1.2.1.12) (GAPDH). |
| M300000465 | 2610301D06Rik | NM_026007 | AK014277 | ELONGATION FACTOR 1-GAMMA (EF-1-GAMMA) (EEF-1B GAMMA). |
| M300019589 | — | — | — | — |
| M300012879 | — | — | AK007389 | SMALL NUCLEAR RIBONUCLEOPROTEIN SM D2 (SNRNP CORE PROTEIN D2) (SM-D2). |

TABLE 4-continued

Genes that distinguish the impact of time in C57B16 mice. Operon Oligo ID can be queried in the OMAD database (http://omad.operon.com)

| Operon Oligo ID | Gene Symbol | RefSeq | Genbank | Description |
|---|---|---|---|---|
| M300006168 | — | NM_177045 | — | — |
| M300002970 | 5730420B22Rik | NM_172597 | AK017582 | — |
| M200009547 | Mybbp1a | NM_016776 | U63648 | MYB BINDING PROTEIN (P160) 1A; NUCLEAR PROTEIN P160. |
| M300021668 | — | — | — | — |
| M300011495 | — | — | BG088667 | SESTRIN 1 (P53-REGULATED PROTEIN PA26). |
| M300017752 | — | — | AF516285 | ANTI-VIPASE LIGHT CHAIN VARIABLE REGION (FRAGMENT). |
| M300007254 | — | NM_172900 | — | — |
| M200006566 | Gga2 | — | AK004632 | — |
| M200006174 | 0610039P13Rik | NM_028752 | BC021548 | — |
| M200000312 | Ly6d | NM_010742 | L40419 | LYMPHOCYTE ANTIGEN LY-6D PRECURSOR (THYMOCYTE B CELL ANTIGEN) (THB). |
| M200000320 | Pou2af1 | NM_011136 | U43788 | POU DOMAIN CLASS 2, ASSOCIATING FACTOR 1 (B-CELL-SPECIFIC COACTIVATOR OBF-1) (OCT BINDING FACTOR 1) (BOB-1) (BOB1) (OCA-B). |
| M200002822 | Blnk | NM_008528 | AJ298054 | B-CELL LINKER; LYMPHOCYTE ANTIGEN 57. |
| M200001144 | Cd79b | NM_008339 | AF002279 | B-CELL ANTIGEN RECEPTOR COMPLEX ASSOCIATED PROTEIN BETA-CHAIN PRECURSOR (B-CELL-SPECIFIC GLYCOPROTEIN B29) (IMMUNOGLOBULIN-ASSOCIATED B29 PROTEIN) (IG-BETA) (CD79B). |
| M200009317 | Scd1 | NM_009127 | BC007474 | ACYL-COA DESATURASE 1 (EC 1.14.19.1) (STEAROYL-COA DESATURASE 1) (FATTY ACID DESATURASE 1) (DELTA(9)-DESATURASE 1). |
| Female C57Bl6 24 hr 50 cGy | | | | |
| M300005062 | BC027756 | NM_145991 | AK080861 | — |
| M200005746 | 1110020J08Rik | NM_025394 | AK003864 | — |
| M200003036 | Nprl2-pending | NM_018879 | BC026548 | G21 PROTEIN. |
| M200004472 | Slc25a1 | NM_153150 | BC037087 | SOLUTE CARRIER FAMILY 25, MEMBER 1; DIGEORGE SYNDROME GENE J; SOLUTE CARRIER FAMILY 25 (MITOCHONDRIAL CARRIER; CITRATE TRANSPORTER) MEMBER 1; TRICARBOXYLATE TRANSPORT PROTEIN PRECURSOR. |
| M200006750 | 2410104I19Rik | NM_133691 | BC010601 | — |
| M200009777 | Aco2 | NM_080633 | BC004645 | ACONITASE 2, MITOCHONDRIAL. |
| M200007587 | E130307M08Rik | NM_026530 | BC017625 | — |
| M200002043 | Mcmd6 | NM_008567 | D86726 | DNA REPLICATION LICENSING FACTOR MCM6 (MIS5 HOMOLOG). |
| M200005598 | Cdk9 | NM_130860 | AF327431 | CYCLIN-DEPENDENT KINASE 9. |
| M200006108 | Coro1b | NM_011778 | AK008947 | CORONIN 1B (CORONIN 2). |
| M300012497 | Rbms2 | NM_019711 | AK054482 | RNA BINDING MOTIF, SINGLE STRANDED INTERACTING PROTEIN 2; SCR3. |
| M200003074 | Psmd3 | NM_009439 | BC003197 | 26S PROTEASOME NON-ATPASE REGULATORY SUBUNIT 3 (26S PROTEASOME REGULATORY SUBUNIT S3) (PROTEASOME SUBUNIT P58) (TRANSPLANTATION ANTIGEN P91A) (TUM-P91A ANTIGEN). |
| M300013135 | — | — | BC034540 | — |
| M300019447 | — | — | BC027368 | — |
| M200009417 | Mt2 | — | K02236 | METALLOTHIONEIN-II (MT-II). |
| M300021033 | Lgals3 | — | X16074 | GALECTIN-3 (GALACTOSE-SPECIFIC LECTIN 3) (MAC-2 ANTIGEN) (IGE-BINDING PROTEIN) (35 KDA LECTIN) (CARBOHYDRATE BINDING PROTEIN 35) (CBP 35) (LAMININ-BINDING PROTEIN) (LECTIN L-29) (L-34 GALACTOSIDE-BINDING LECTIN). |
| M300004485 | P4hb | — | J05185 | PROTEIN DISULFIDE ISOMERASE PRECURSOR (PDI) (EC 5.3.4.1) (PROLYL 4-HYDROXYLASE BETA SUBUNIT) (CELLULAR THYROID HORMONE BINDING PROTEIN) (P55) (ERP59). |
| M200012720 | — | — | BC008093 | EUKARYOTIC TRANSLATION INITIATION FACTOR 5A (EIF-5A) (EIF-4D) (REV-BINDING FACTOR). |
| M200006860 | — | NM_010312 | U38505 | GUANINE NUCLEOTIDE-BINDING PROTEIN G(I)/G(S)/G(T) BETA SUBUNIT 2 (TRANSDUCIN BETA CHAIN 2) (G PROTEIN BETA 2 SUBUNIT). |

TABLE 4-continued

Genes that distinguish the impact of time in C57B16 mice. Operon Oligo ID can be queried in the OMAD database (http://omad.operon.com)

| Operon Oligo ID | Gene Symbol | RefSeq | Genbank | Description |
|---|---|---|---|---|
| M300011574 | — | — | — | — |
| M300015461 | — | — | — | — |
| M300021713 | — | — | — | — |
| M200009655 | Cct6a | NM_009838 | AB022159 | T-COMPLEX PROTEIN 1, ZETA SUBUNIT (TCP-1-ZETA) (CCT-ZETA) (CCT-ZETA-1). |
| M300004979 | Fn1 | — | BC004724 | — |
| M200014015 | Lgals1 | NM_008495 | AK004298 | GALECTIN-1 (BETA-GALACTOSIDE-BINDING LECTIN L-14-I) (LACTOSE-BINDING LECTIN 1) (S-LAC LECTIN 1) (GALAPTIN) (14 KDA LECTIN). |
| Female C57BI6 24 hr 200 cGy | | | | |
| M300010249 | Txk | NM_013698 | L35268 | TYROSINE-PROTEIN KINASE TXK (EC 2.7.1.112) (PTK-RL-18) (RESTING LYMPHOCYTE KINASE). |
| M300010028 | — | — | BC026557 | SIMILAR TO PTD015 PROTEIN. |
| M200009777 | Aco2 | NM_080633 | BC004645 | ACONITASE 2, MITOCHONDRIAL. |
| M200005598 | Cdk9 | NM_130860 | AF327431 | CYCLIN-DEPENDENT KINASE 9. |
| M200000327 | Cct7 | NM_007638 | AB022160 | T-COMPLEX PROTEIN 1, ETA SUBUNIT (TCP-1-ETA) (CCT-ETA). |
| M200003578 | Bpnt1 | NM_011794 | AF125043 | BISPHOSPHATE 3'-NUCLEOTIDASE 1. |
| M200002251 | Akr1b8 | NM_008012 | U04204 | ALDOSE REDUCTASE-RELATED PROTEIN 1 (EC 1.1.1.21) (AR) (ALDEHYDE REDUCTASE) (VAS DEFERENS ANDROGEN-DEPENDENT PROTEIN) (MVDP) (ALDO-KETO REDUCTASE FAMILY 1 MEMBER B7). |
| M200012683 | Acat2 | — | BC012496 | T-COMPLEX PROTEIN (TCP-1X) (FRAGMENT). |
| M300002824 | Hnrpk | NM_025279 | BC006694 | HETEROGENEOUS NUCLEAR RIBONUCLEOPROTEIN K (HNRNP K) (65 KDA PHOSPHOPROTEIN). |
| M200007603 | 0610009O03Rik | NM_026660 | AK089055 | — |
| M200006373 | Nars | — | AK013880 | — |
| M200002442 | Cdk4 | NM_009870 | X65069 | CELL DIVISION PROTEIN KINASE 4 (EC 2.7.1.—) (CYCLIN-DEPENDENT KINASE 4) (PSK-J3) (CRK3). |
| M200006712 | Shmt2 | NM_028230 | BC004825 | — |
| M200002501 | Lrp1 | NM_008512 | AF367720 | LOW DENSITY LIPOPROTEIN RECEPTOR-RELATED PROTEIN 1; LOW DENSITY LIPOPROTEIN RECEPTOR RELATED PROTEIN; LOW DENSITY LIPOPROTEIN RECEPTOR RELATED PROTEIN 1. |
| M200006860 | — | NM_010312 | U38505 | GUANINE NUCLEOTIDE-BINDING PROTEIN G(I)/G(S)/G(T) BETA SUBUNIT 2 (TRANSDUCIN BETA CHAIN 2) (G PROTEIN BETA 2 SUBUNIT). |
| M300004485 | P4hb | — | J05185 | PROTEIN DISULFIDE ISOMERASE PRECURSOR (PDI) (EC 5.3.4.1) (PROLYL 4-HYDROXYLASE BETA SUBUNIT) (CELLULAR THYROID HORMONE BINDING PROTEIN) (P55) (ERP59). |
| M200012927 | Angptl2 | NM_011923 | AF125176 | ANGIOPOIETIN-RELATED PROTEIN 2 PRECURSOR (ANGIOPOIETIN-LIKE 2). |
| M300011172 | — | — | — | — |
| M200002468 | Alad | NM_008525 | X13752 | DELTA-AMINOLEVULINIC ACID DEHYDRATASE (EC 4.2.1.24) (PORPHOBILINOGEN SYNTHASE) (ALADH). |
| M300004916 | Col3a1 | — | X57983 | COLLAGEN ALPHA 1(III) CHAIN PRECURSOR. |
| M200000033 | Idb3 | NM_008321 | M60523 | DNA-BINDING PROTEIN INHIBITOR ID-3 (ID-LIKE PROTEIN INHIBITOR HLH 462). |
| M200003353 | Anxa1 | NM_010730 | M24554 | ANNEXIN I (LIPOCORTIN I) (CALPACTIN II) (CHROMOBINDIN 9) (P35) (PHOSPHOLIPASE A2 INHIBITORY PROTEIN). |
| M200014015 | Lgals1 | NM_008495 | AK004298 | GALECTIN-1 (BETA-GALACTOSIDE-BINDING LECTIN L-14-I) (LACTOSE-BINDING LECTIN 1) (S-LAC LECTIN 1) (GALAPTIN) (14 KDA LECTIN). |
| M200000992 | Bgn | NM_007542 | Y11758 | BIGLYCAN PRECURSOR (BONE/CARTILAGE PROTEOGLYCAN I) (PG-S1). |
| M200003310 | AU044919 | — | BC010327 | IG GAMMA-2B CHAIN C REGION, MEMBRANE-BOUND FORM. |
| Female C57BI6 24 hr 1000 cGy | | | | |
| M300000233 | Capns1 | NM_009795 | BC018352 | CALCIUM-DEPENDENT PROTEASE, SMALL SUBUNIT (CALPAIN REGULATORY SUBUNIT) |

TABLE 4-continued

Genes that distinguish the impact of time in C57B16 mice. Operon Oligo ID can be queried in the OMAD database (http://omad.operon.com)

| Operon Oligo ID | Gene Symbol | RefSeq | Genbank | Description |
| --- | --- | --- | --- | --- |
| | | | | (CALCIUM-ACTIVATED NEUTRAL PROTEINASE) (CANP). |
| M300001059 | D0H8S2298E | — | BC024492 | REPRODUCTION 8 (DNA SEGMENT, HUMAN S2298E). |
| M300013845 | Atpaf2 | NM_145427 | BC013607 | ATP SYNTHASE MITOCHONDRIAL F1 COMPLEX ASSEMBLY FACTOR 2. |
| M300004022 | Ermelin-pending | NM_139143 | AB071697 | ENDOPLASMIC RETICULUM MEMBRANE PROTEIN; EXPRESSED SEQUENCE AI853222. |
| M200004159 | Nono | NM_023144 | AK013444 | NON-POU-DOMAIN-CONTAINING, OCTAMER BINDING PROTEIN; NON-POU-DOMAIN-CONTAINING, OCTAMER-BINDING PROTEIN. |
| M200003982 | Golga5 | NM_013747 | AF026274 | GOLGI AUTOANTIGEN, GOLGIN SUBFAMILY A, 5. |
| M200000385 | Slc1a7 | NM_009201 | D85044 | NEUTRAL AMINO ACID TRANSPORTER B (INSULIN-ACTIVATED AMINO ACID TRANSPORTER) (ASC-LIKE NA(+) DEPENDENT NEUTRAL AMINO ACID TRANSPORTER ASCT2). |
| M300006374 | Psmc2 | — | BC005462 | 26S PROTEASE REGULATORY SUBUNIT 7 (MSS1 PROTEIN). |
| M200004383 | Cse1l | NM_023565 | AF301152 | IMPORTIN-ALPHA RE-EXPORTER (CHROMOSOME SEGREGATION 1-LIKE PROTEIN) (CELLULAR APOPTOSIS SUSCEPTIBILITY PROTEIN). |
| M200005955 | 1810019E15Rik | — | AK007546 | — |
| M200005912 | Narg1 | NM_053089 | BC030167 | NMDA RECEPTOR-REGULATED GENE 1; N-TERMINAL ACEYLTRANSFERASE 1. |
| M200001798 | Lbr | NM_133815 | BC042522 | LAMIN B RECEPTOR; ICHTHYOSIS. |
| M200015331 | AV278559 | NM_134152 | AB071194 | — |
| M300022323 | — | — | — | — |
| M300021610 | — | — | — | — |
| M300017722 | — | NM_024266 | X62482 | 40S RIBOSOMAL PROTEIN S25. |
| M200003662 | Hprt | NM_013556 | K01514 | HYPDXANTHINE-GUANINE PHOSPHORIBOSYLTRANSFERASE (EC 2.4.2.8) (HGPRT) (HGPRTASE) (HPRT B). |
| M300004429 | Blnk | NM_008528 | AJ222814 | B-CELL LINKER; LYMPHOCYTE ANTIGEN 57. |
| M300018162 | — | — | — | — |
| M300013112 | — | — | J00595 | IG LAMBDA-2 CHAIN C REGION. |
| M300011693 | — | — | — | — |
| M300000425 | Rps11 | NM_013725 | AK005147 | 40S RIBOSOMAL PROTEIN S11. |
| M300017758 | — | NM_027015 | — | RIBOSOMAL PROTEIN S27. |
| M300004265 | Ms4a1 | NM_007641 | AK017903 | B-CELL SURFACE PROTEIN CD20 HOMOLOG (B-CELL DIFFERENTIATION ANTIGEN LY-44). |
| M300020997 | — | — | — | — |
| Female C57BI6 day 7 50 cGy | | | | |
| M300007861 | Gypa | NM_010369 | M73815 | GLYCOPHORIN. |
| M200006628 | W64236 | NM_144805 | BC019416 | — |
| M300005566 | Capn3 | NM_007601 | AF091998 | CALPAIN 3 LARGE SUBUNIT (EC 3.4.22.17) (CALPAIN L3) (CALPAIN P94, LARGE SUBUNIT) (CALCIUM-ACTIVATED NEUTRAL PROTEINASE 3) (CANP 3) (MUSCLE-SPECIFIC CALCIUM-ACTIVATED NEUTRAL PROTEASE 3 LARGE SUBUNIT). |
| M200001376 | Gp5 | NM_008148 | Z69595 | PLATELET GLYCOPROTEIN V PRECURSOR (GPV) (CD42D). |
| M200005863 | Nup210 | NM_018815 | AF113751 | NUCLEOPORIN 210; NUCLEAR PORE MEMBRANE GLYCOPROTEIN 210; NUCLEAR PORE MEMBRANE PROTEIN 210. |
| M200007831 | 4933407D05Rik | NM_029748 | AK016715 | — |
| M200001259 | Cnih | NM_009919 | AF022811 | CORNICHON HOMOLOG. |
| M200000413 | Hdgf | NM_008231 | BC021654 | HEPATOMA-DERIVED GROWTH FACTOR (HDGF). |
| M200003736 | Prdx4 | NM_016764 | U96746 | PEROXIREDOXIN 4 (EC 1.11.1.—) (PRX-IV) (THIOREDOXIN PEROXIDASE AO372) (THIOREDOXIN-DEPENDENT PEROXIDE REDUCTASE A0372) (ANTIOXIDANT ENZYME AOE372). |
| M300003493 | — | — | BC028899 | PEPTIDYL-PROLYL CIS-TRANS ISOMERASE LIKE 2 (EC 5.2.1.8) (PPIASE) (ROTAMASE) (CYCLOPHILIN-60) (CYCLOPHILIN-LIKE PROTEIN CYP-60). |
| M300020830 | — | — | — | — |

TABLE 4-continued

Genes that distinguish the impact of time in C57B16 mice. Operon Oligo ID can be queried in the OMAD database (http://omad.operon.com)

| Operon Oligo ID | Gene Symbol | RefSeq | Genbank | Description |
| --- | --- | --- | --- | --- |
| M200004428 | 0610016L08Rik | NM_029787 | BC032013 | DIAPHORASE 1 (NADH). |
| M200006257 | 2610312E17Rik | NM_027432 | AK050391 | — |
| M200009010 | AI840044 | NM_144895 | BC022921 | — |
| M300001264 | 1810036I24Rik | NM_026210 | AK077277 | — |
| M300013796 | Shc1 | NM_011368 | U15784 | SHC TRANSFORMING PROTEIN. |
| M300021114 | 9130413I22Rik | NM_026242 | AB041651 | — |
| M300018312 | — | — | — | — |
| M300003187 | — | — | — | — |
| M300001659 | Kpna2 | NM_010655 | BC006720 | IMPORTIN ALPHA-2 SUBUNIT (KARYOPHERIN ALPHA-2 SUBUNIT) (SRP1-ALPHA) (RAG COHORT PROTEIN 1) (PENDULIN) (PORE TARGETING COMPLEX 58 KDA SUBUNIT) (PTAC58) (IMPORTIN ALPHA P1). |
| M300011584 | — | — | — | — |
| M300018684 | Kpna2 | NM_010655 | BC006720 | IMPORTIN ALPHA-2 SUBUNIT (KARYOPHERIN ALPHA-2 SUBUNIT) (SRP1-ALPHA) (RAG COHORT PROTEIN 1) (PENDULIN) (PORE TARGETING COMPLEX 58 KDA SUBUNIT) (PTAC58) (IMPORTIN ALPHA P1). |
| M300005759 | Ube2v1 | — | BC019372 | SIMILAR TO UBIQUITIN-CONJUGATING ENZYME E2 VARIANT 1 (EC 6.3.2.19) (UBIQUITIN-PROTEIN LIGASE) (UBIQUITIN CARRIER PROTEIN). |
| M200014015 | Lgals1 | NM_008495 | AK004298 | GALECTIN-1 (BETA-GALACTOSIDE-BINDING LECTIN L-14-I) (LACTOSE-BINDING LECTIN 1) (S-LAC LECTIN 1) (GALAPTIN) (14 KDA LECTIN). |
| M200000746 | Calr | NM_007591 | M92988 | CALRETICULIN PRECURSOR (CRP55) (CALREGULIN) (HACBP) (ERP60). |
| Female C57Bl6 day 7 200 Gy | | | | |
| M200004758 | Blvrb | NM_144923 | BC027279 | BILIVERDIN REDUCTASE B (FLAVIN REDUCTASE (NADPH)). |
| M300003852 | Treml1-pending | — | AK017256 | — |
| M300007590 | — | NM_172479 | — | — |
| M300005240 | Mgst3 | NM_025569 | BC029669 | MICROSOMAL GLUTATHIONE S-TRANSFERASE 3. |
| M200000621 | Gpc4 | NM_008150 | X83577 | GLYPICAN-4 PRECURSOR (K-GLYPICAN). |
| M300006292 | 1810017F10Rik | NM_025452 | AK008935 | BETA-CASEIN-LIKE. |
| M300004473 | 4833406P10Rik | — | AF404774 | ACTIN-BINDING LIM PROTEIN 1 MEDIUM ISOFORM. |
| M300005665 | 2010011I20Rik | NM_025912 | BC016210 | — |
| M200015276 | Pep4 | NM_008820 | D82983 | XAA-PRO DIPEPTIDASE (EC 3.4.13.9) (X-PRO DIPEPTIDASE) (PROLINE DIPEPTIDASE) (PROLIDASE) (IMIDODIPEPTIDASE) (PEPTIDASE 4). |
| M300000073 | Myf5 | NM_008656 | X56182 | MYOGENIC FACTOR MYF-5. |
| M300002998 | Nisch | NM_022656 | AF315344 | NISCHARIN; IMIDAZOLINE RECEPTOR I-1-LIKE PROTEIN. |
| M300008241 | 1110005A05Rik | NM_025372 | AK003451 | — |
| M300002598 | — | — | AF206023 | ANTI-MYOSIN IMMUNOGLOBULIN HEAVY CHAIN VARIABLE REGION (FRAGMENT). |
| M200004350 | — | — | BC024401 | SIMILAR TO DC12 PROTEIN. |
| M300007147 | — | — | — | — |
| M200009417 | Mt2 | — | K02236 | METALLOTHIONEIN-II (MT-II). |
| M300022215 | — | — | — | — |
| M200014231 | Supt16h | NM_033618 | AF323667 | SUPPRESSOR OF TY 16 HOMOLOG; SUPPRESSOR OF TY 16 HOMOLOG (*S. CEREVISIAE*). |
| M300016699 | — | — | AK011630 | — |
| M300015461 | — | — | — | — |
| M300006903 | — | NM_007624 | — | CHROMOBOX HOMOLOG 3 (DROSOPHILA HP1 GAMMA); HETEROCHROMATIN PROTEIN 1 GAMMA. |
| M300002502 | Pnn | NM_008891 | Y08701 | PININ; DNA SEGMENT, CHR 12, ERATO DOI 512, EXPRESSED. |
| M200000746 | Calr | NM_007591 | M92988 | CALRETICULIN PRECURSOR (CRP55) (CALREGULIN) (HACBP) (ERP60). |
| M200009655 | Cct6a | NM_009838 | AB022159 | T-COMPLEX PROTEIN 1, ZETA SUBUNIT (TCP-1-ZETA) (CCT-ZETA) (CCT-ZETA-1). |
| M300011584 | — | — | — | — |

Specificity of PB Signatures

Figure 5B:
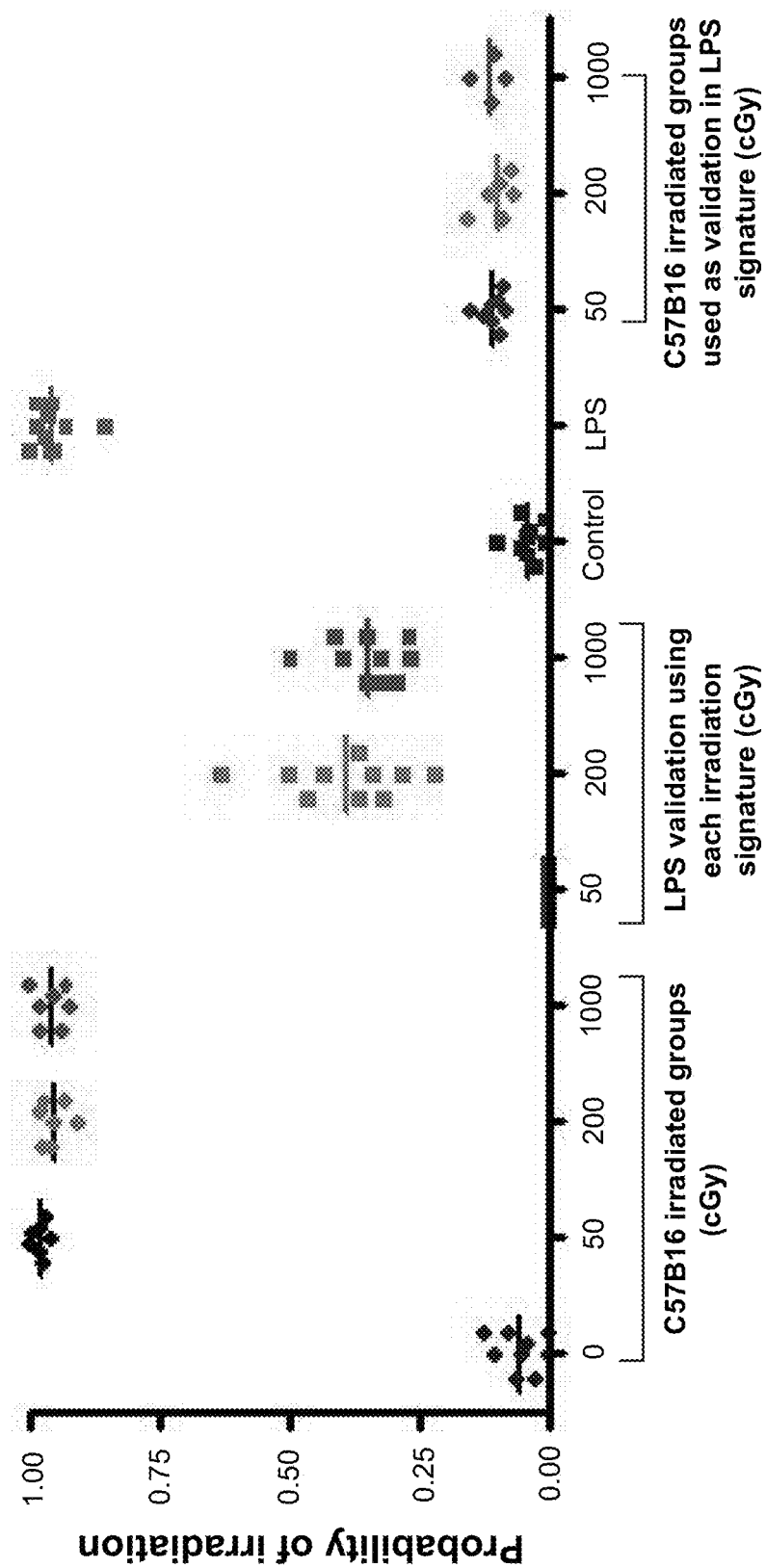

In addition to inter-individual variations (Whitney et al, Proc. Natl. Acad. Sci. USA 101:1896-1901 (2003)), human populations are heterogeneous with respect to health status and medical conditions. Therefore, it is critical to determine whether PB gene expression profiles of radiation response are specific to radiation exposure itself or whether these signatures are potentially confounded by other genotoxic stresses. The choice was made to compare the PB gene expression response to ionizing radiation exposure with that of gram-negative bacterial sepsis, since this syndrome can be expected to induce similar multiorgan toxicity as is observed following radiation injury (Wasalenko et al, Ann. Int. Med. 140:1037-1051 (2004), Mettler et al, N. Engl. J. Med. 346:1554-1561 (2002), Dainiak, Exp. Hematol. 30:513-528 (2002), Inoue et al, FASEB J. 20:533-535 (2006)). A pattern of gene expression could be identified which effectively distinguished female C57Bl6 mice treated with *Escherichia coli*-derived lipopolysaccharide (LPS), experiencing sepsis syndrome, from untreated female C57Bl6 mice (FIG. 5A). Applying a leave-one-out cross-validation analysis, it was found that the PB signature for 50 cGy irradiation in C57Bl6 mice correctly predicted the status of all LPS-treated C57Bl6 mice as non-irradiated, suggesting robust specificity of the signature for low level (50 cGy) irradiation and sepsis syndrome (FIG. 5B). The PB signatures for 200 cGy and 1000 cGy also correctly predicted the LPS-treated mice as non-irradiated, although these probabilities were less robust than the application of the 50 cGy signature (FIG. 5B). The PB signature of LPS-treatment also correctly predicted the status of all irradiated mice as "non-LPS treated" (FIG. 5B, right). These data indicate that the PB gene expression profiles of radiation response and bacterial sepsis are quite specific and able to distinguish one condition from the other with a high level of accuracy. No overlap was observed between the genes which comprised the PB signature of LPS-sepsis and the PB signatures of radiation exposure in C57Bl6 mice (Table 5).

TABLE 5

Genes that distinguish LPS treatment in C57Bl6 mice. Operon Oligo ID can be queried in the OMAD database (http://omad.operon.com)

| Operon Oligo ID | Gene Symbol | RefSeq | Genbank | Description |
| --- | --- | --- | --- | --- |
| M200003295 | Saa3 | NM_011315 | M17792 | SERUM AMYLOID A-3 PROTEIN PRECURSOR. |
| M300009870 | Ccl12 | NM_011331 | AF065938 | SMALL INDUCIBLE CYTOKINE A12 PRECURSOR (CCL12) (MONOCYTE CHEMOTACTIC PROTEIN 5) (MCP-5) (MCP-1 RELATED CHEMOKINE). |
| M300005418 | Il1rn | NM_031167 | S64082 | INTERLEUKIN-1 RECEPTOR ANTAGONIST PROTEIN PRECURSOR (IL-1RA) (IL-1RN) (IRAP). |
| M200001838 | Upp | NM_009477 | D44464 | URIDINE PHOSPHORYLASE (EC 2.4.2.3) (UDRPASE). |
| M200000053 | Fcgr1 | NM_010186 | BC025535 | HIGH AFFINITY IMMUNOGLOBULIN GAMMA FC RECEPTOR I PRECURSOR (FC-GAMMA RI) (FCRI) (IGG FC RECEPTOR I). |
| M200004157 | 9130009C22Rik | NM_027835 | AF374384 | — |
| M300005305 | Lcn2 | — | X81627 | NEUTROPHIL GELATINASE-ASSOCIATED LIPOCALIN PRECURSOR (NGAL) (P25) (SV-40 INDUSED 24P3 PROTEIN) (LIPOCALIN 2). |
| M300006479 | Bst1 | NM_009763 | D31788 | ADP-RIBOSYL CYCLASE 2 PRECURSOR (EC 3.2.2.5) (CYCLIC ADP-RIBOSE HYDROLASE 2) (CADPR HYDROLASE 2) (BONE MARROW STROMAL ANTIGEN 1) (BST-1) (BP-3 ALLOANTIGEN) (ANTIGEN BP3). |
| M200004765 | Gbp2 | NM_010260 | AF077007 | GUANYLATE NUCLEOTIDE BINDING PROTEIN 2. |
| M300005673 | Zbp1 | NM_021394 | BC020033 | Z-DNA BINDING PROTEIN 1 (TUMOR STROMA AND ACTIVATED MACROPHAGE PROTEIN DLM-1). |
| M300005674 | Zbp1 | NM_021394 | BC020033 | Z-DNA BINDING PROTEIN 1 (TUMOR STROMA AND ACTIVATED MACROPHAGE PROTEIN DLM-1). |
| M300001891 | Gp49b | NM_013532 | U05264 | MAST CELL SURFACE GLYCOPROTEIN GP49B PRECURSOR. |
| M300005166 | Ifi204 | NM_008329 | M31419 | INTERFERON-ACTIVATABLE PROTEIN 204 (IFI-204) (INTERFERON-INDUCIBLE PROTEIN P204). |
| M200005576 | Usp18 | NM_011909 | AF069502 | UBL CARBOXYL-TERMINAL HYDROLASE 18 (EC 3.1.2.—) (UBL THIOLESTERASE 18) (ISG15-SPECIFIC PROCESSING PROTEASE) (43 KDA ISG15-SPECIFIC PROTEASE). |
| M300020771 | — | — | — | — |
| M300011591 | — | NM_172893 | BC024579 | — |
| M200007439 | Gtpi-pending | NM_019440 | AJ007972 | INTERFERON-G INDUCED GTPASE. |
| M300012693 | — | — | — | — |
| M300012210 | — | — | — | — |
| M200014281 | 2010008K16Rik | NM_027320 | BC008158 | INTERFERON-INDUCED 35 KDA PROTEIN HOMOLOG (IFP 35). |
| M300009340 | — | NM_145481 | BC021340 | — |
| M200004564 | Nte | NM_015801 | AF173829 | NEUROPATHY TARGET ESTERASE; SWISS CHEESE. |
| M300000152 | Araf | NM_009703 | D00024 | A-RAF PROTO-ONCOGENE SERINE/THREONINE-PROTEIN KINASE (EC 2.7.1.—). |
| M200006264 | — | NM_176831 | — | — |
| M300000077 | D15Ertd417e | NM_144811 | BC021398 | CHROMOBOX PROTEIN HOMOLOG 6. |

PB Signatures of Radiation and Chemotherapy are Specific in Humans

Figure 6A:
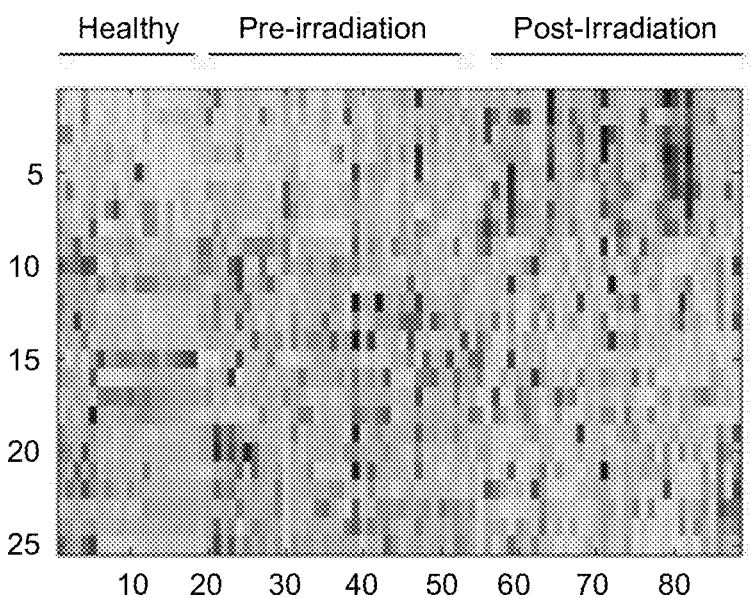
FIGS. 6A-6D. PB metagene profiles of human radiation exposure and chemotherapy treatment are accurate and specific relative to each other.

In order to extend the analysis of PB signature specificity to humans, PB was collected from a population of healthy individuals (n=18), patients who had undergone total body irradiation as conditioning prior to hematopoietic stem cell transplantation (n=47) and patients who had undergone alkylator-based chemotherapy conditioning alone (n=41). RNA of sufficient quality was available from 18 healthy donor samples, 36 pre-irradiated patients, 34 post-irradiated patients, 36 pre-chemotherapy treatment patients and 32 post-chemotherapy patients (Table 6). A supervised binary regression analysis identified a metagene profile of 25 genes that distinguished the healthy individuals and the non-irradiated patients from the irradiated patients (FIG. 6A). A leave-one-out cross validation analysis demonstrated that this PB predictor of human radiation response was 100% accurate in predicting the healthy individuals and the non-irradiated patients and 91% accurate at predicting the irradiated patients (FIG. 6A).

TABLE 6

Donor Patient Characteristics

| Characteristic | Number |
| --- | --- |
| Samples analyzed | n = 18 healthy donors |
|  | n = 36 patients pre-radiotherapy |
|  | n = 34 patients post-radiotherapy |
|  | n = 36 patients pre-chemotherapy |
|  | n = 32 patients post-chemotherapy |
| Patient/Donor Age | 47.9 years (mean) |
| Diagnoses | MDS/AML (n = 23) |
|  | ALL (n = 8) |
|  | Multiple myeloma (n = 20) |
|  | Non-Hodgkin's Lymphoma (n = 20) |
|  | Hodgkin's Disease (n = 6) |
|  | Myeloproliferative disorder (n = 7) |
|  | Scleroderma (n = 3) |
|  | Sickle cell disease (n = 1) |
| Prior radiotherapy | n = 15 |
| Prior chemotherapy | n = 82 |
| Transplantation type | Non-myeloablative allogeneic/200 cGy (n = 24) |
|  | Myeloablative allogeneic/1350 cGy (n = 15) |
|  | Myeloablative autologous/1200 cGy (n = 8) |

TABLE 6-continued

Donor Patient Characteristics

| Characteristic | Number |
| --- | --- |
|  | Chemotherapy allogeneic (n = 19) |
|  | Chemotherapy autologous (n = 22) |

Figure 6B:
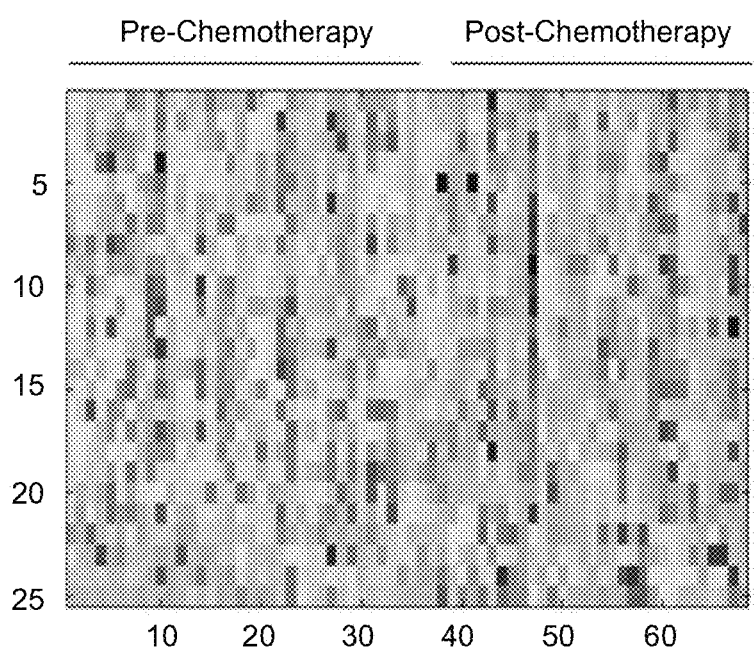
Figure 6C:
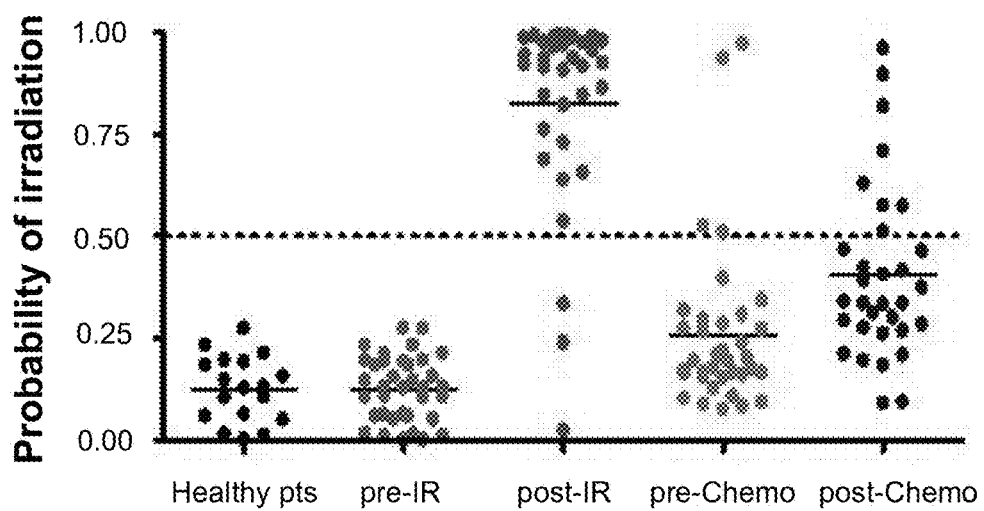
Figure 6D:
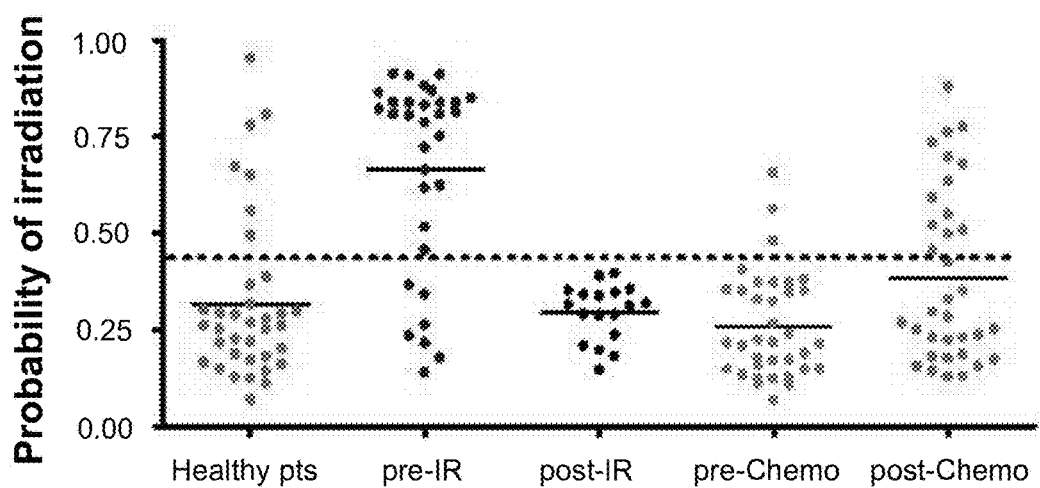

Patients undergoing either TBI-based or chemotherapy-based conditioning followed by allogeneic or autologous stem cell transplantation were eligible for enrollment. PB samples were collected prior to and 6 hours following either 200 cGy total body irradiation (non-myeloablative conditioning) or the first fraction (150 cGy) of total body irradiation (myeloablative conditioning).
MDS = myelodysplastic syndrome,
AML = acute myelogenous leukemia,
ALL = acute lymphocytic leukemia In order to test the specificity of this PB signature of human radiation response, its accuracy was next tested in predicting the status of patients who had undergone chemotherapy treatment alone. This signature correctly predicted 89% of the non-irradiated, pre-chemotherapy patients as non-irradiated and 75% of the chemotherapy-treated patients as non-irradiated (FIG. 6A). Interestingly, 2 of the post-chemotherapy patients had a prior history of total lymphoid irradiation and both of these were mispredicted as "irradiated", suggesting perhaps that a durable molecular response to radiation was evident in these patients. Considering the entire population, the overall accuracy of the PB predictor of radiation was 90%. Within the chemotherapy-treated patients, a PB signature could be identified that appeared to distinguish untreated patients from chemotherapy-treated patients (FIG. 6B). A leave-one-out cross-validation analysis demonstrated that this PB signature of chemotherapy treatment was 81% accurate at distinguishing the untreated patients and 78% accurate at predicting the chemotherapy-treated patients (FIG. 6B). Furthermore, the chemotherapy metagene profile demonstrated 100% accuracy in predicting the status of healthy individuals, 92% accuracy in predicting the non-irradiated patients, and 62% accuracy in predicting the PB samples from irradiated patients as not having received chemotherapy (FIG. 6B). The overall accuracy of the PB predictor of chemotherapy-treatment was 81%. Interestingly, no overlapping genes were identified between the PB signature of radiation and the PB signature of chemotherapy treatment (Tables 7 and 8). It is also worth noting that all 12 of the post-irradiation patients whose status was mispredicted by the PB chemotherapy signature had received prior chemotherapy in the treatment of their underlying disease.

TABLE 7

Genes that distinguish radiation status in humans. Operon Oligo ID can be queried in the OMAD database (http://omad.operon.com)

| Operon Oligo_ID | Gene Symbol | RefSeq | Genbank | Description |
| --- | --- | --- | --- | --- |
| H200000088 | XPC | NM_004628 | X65024 | DNA-REPAIR PROTEIN COMPLEMENTING XP-C CELLS (XERODERMA PIGMENTOSUM GROUP C COMPLEMENTING PROTEIN) (P125) |
| H200001266 | — | NM_017792 | AK000380 | — |
| H200002100 | — | NM_024556 | BC001340 | — |
| H200002529 | — | NM_032324 | AF416713 | — |
| H200004865 | — | NM_006828 | AL834463 | DJ467N11.1 PROTEIN |
| H200006009 | GTF3A | NM_002097 | U14134 | TRANSCRIPTION FACTOR IIIA (FACTOR A) (TFIIIA) |
| H200006598 | PCNA | NM_002592 | BC000491 | PROLIFERATING CELL NUCLEAR ANTIGEN (PCNA) (CYCLIN) |
| H200008365 | CDKN1A | NM_000389 | BC013967 | CYCLIN-DEPENDENT KINASE INHIBITOR 1 (P21) (CDK-INTERACTING PROTEIN 1) (MELANOMA DIFFERENTIATION ASSOCIATED PROTEIN 6) (MDA-6) |

TABLE 7-continued

Genes that distinguish radiation status in humans. Operon Oligo ID can be queried in the OMAD database (http://omad.operon.com)

| Operon Oligo_ID | Gene Symbol | RefSeq | Genbank | Description |
|---|---|---|---|---|
| H200011100 | PPM1D | NM_003620 | BC033893 | PROTEIN PHOSPHATASE 2C DELTA ISOFORM (PP2C-DELTA) (P53-INDUCED PROTEIN PHOSPHATASE 1) (PROTEIN PHOSPHATASE MAGNESIUM-DEPENDENT 1 DELTA) |
| H200011577 | — | NM_018247 | AK001718 | — |
| H200014322 | — | — | BC009552 | CGI-203 |
| H200014719 | ACTA2 | NM_001613 | X60732 | ACTIN, AORTIC SMOOTH MUSCLE (ALPHA-ACTIN 2) |
| H200016323 | — | NM_152240 | BC002896 | P53 TARGET ZINC FINGER PROTEIN ISOFORM 1; ZINC FINGER PROTEIN WIG1; WIG-1/PAG608 PROTEIN |
| H200017549 | TIMM8B | NM_012459 | BC000711 | MITOCHONDRIAL IMPORT INNER MEMBRANE TRANSLOCASE SUBUNIT TIM8 B (DEAFNESS DYSTONIA PROTEIN 2) (DDP-LIKE PROTEIN) |
| H300000421 | — | NM_016399 | BC002638 | PROTEIN 15E1.1 (PROTEIN HSPC132) |
| H300003103 | — | — | — | — |
| H300003151 | MOAP1 | NM_022151 | BC015044 | MODULATOR OF APOPTOSIS 1; MAP-1 PROTEIN; PARANEOPLASTIC ANTIGEN LIKE 4 |
| H300010830 | — | NM_022767 | BC005164 | — |
| H300015667 | — | NM_022767 | BC005164 | — |
| H300018970 | — | NM_014454 | AK001886 | SESTRIN 1 (P53-REGULATED PROTEIN PA26) |
| H300019371 | DDB2 | NM_000107 | BC000093 | DNA DAMAGE BINDING PROTEIN 2 (DAMAGE-SPECIFIC DNA BINDING PROTEIN 2) (DDB P48 SUBUNIT) (DDBB) (UV-DAMAGED DNA-BINDING PROTEIN 2) (UV-DDB 2) |
| H300020184 | C19orf2 | NM_003796 | AB006572 | RNA POLYMERASE II SUBUNIT 5-MEDIATING PROTEIN (RPB5-MEDIATING PROTEIN) |
| H300020858 | HNRPDL | NM_005463 | BC011714 | HETEROGENEOUS NUCLEAR RIBONUCLEOPROTEIN D-LIKE; A + U-RICH ELEMENT RNA BINDING FACTOR |
| H300021118 | BBC3 | NM_014417 | AF354655 | BCL2 BINDING COMPONENT 3; BCL-2 BINDING COMPONENT 3; PUMA/JFY1 PROTEIN; BCL-2 BINDING COMPONENT 3 |
| H300022025 | BAX | NM_138763 | U19599 | BAX PROTEIN, CYTOPLASMIC ISOFORM DELTA |

TABLE 8

Genes that distinguish chemotherapy treatment in humans. Operon Oligo ID can be queried in the OMAD database (http://omad.operon.com)

| Operon oligo_ID | Gene Symbol | RefSeq | Genbank | Description |
|---|---|---|---|---|
| H200001454 | FKBP5 | NM_004117 | U42031 | FK506-BINDING PROTEIN 5 (EC 5.2.1.8) (PEPTIDYL-PROLYL CIS-TRANS ISOMERASE) (PPIASE) (ROTAMASE) (51 KDA FK506-BINDING PROTEIN) (FKBP-51) (54 KDA PROGESTERONE RECEPTOR-ASSOCIATED IMMUNOPHILIN) (FKBP54) (P54) (FF1 ANTIGEN) (HSP90-BINDING IMMUNOPHILIN) |
| H200002954 | SAP30 | NM_003864 | BC016757 | SIN3 ASSOCIATED POLYPEPTIDE P30; SIN3-ASSOCIATED POLYPEPTIDE, 30 KD |
| H200004993 | SOCS1 | NM_003745 | AB000676 | SUPPRESSOR OF CYTOKINE SIGNALING 1 (SOCS-1) (JAK-BINDING PROTEIN) (JAB) (STAT INDUCED STAT INHIBITOR 1) (SSI-1) (TEC-INTERACTING PROTEIN 3) (TIP-3) |
| H200002479 | CRAMP1L | — | AB037847 | — |
| H200020334 | — | NM_006372 | AY034482 | NS1-ASSOCIATED PROTEIN 1 |
| H200002535 | — | NM_018034 | BC025315 | — |
| H200002231 | UVRAG | NM_003369 | AB012958 | UV RADIATION RESISTANCE-ASSOCIATED GENE PROTEIN (P63) |
| H200002230 | — | NM_005475 | AJ012793 | LYMPHOCYTE SPECIFIC ADAPTER PROTEIN LNK (SIGNAL TRANSDUCTION PROTEIN LNK) (LYMPHOCYTE ADAPTER PROTEIN) |
| H300001588 | ASGR1 | NM_001671 | AB070933 | ASIALOGLYCOPROTEIN RECEPTOR 1 (HEPATIC LECTIN H1) (ASGPR) (ASGP-R) |
| H300001821 | BLVRA | NM_000712 | AC005189 | BILIVERDIN REDUCTASE A PRECURSOR (EC 1.3.1.24) (BILIVERDIN-IX ALPHA-REDUCTASE) |
| H200001397 | RAI17 | — | AB033050 | — |

TABLE 8-continued

Genes that distinguish chemotherapy treatment in humans. Operon Oligo ID can be queried in the OMAD database (http://omad.operon.com)

| Operon oligo_ID | Gene Symbol | RefSeq | Genbank | Description |
| --- | --- | --- | --- | --- |
| H300008401 | TRAF3 | NM_003300 | U15637 | TNF RECEPTOR ASSOCIATED FACTOR 3 (CD40 RECEPTOR ASSOCIATED FACTOR 1) (CRAF1) (CD40 BINDING PROTEIN) (CD40BP) (LMP1 ASSOCIATED PROTEIN) (LAP1) (CAP-1) |
| H300022877 | LILRB1 | NM_006669 | AF009221 | LEUKOCYTE IMMUNOGLOBULIN-LIKE RECEPTOR, SUBFAMILY B (WITH TM AND ITIM DOMAINS), MEMBER 1; LEUKOCYTE IMMUNOGLOBULIN-LIKE RECEPTOR 1; CD85 ANTIGEN |
| H300018428 | BID | NM_001196 | BC022072 | BH3 INTERACTING DOMAIN DEATH AGONIST (BID) |
| H300022441 | — | — | AL360143 | — |
| H200014949 | HMOX1 | NM_002133 | X14782 | HEME OXYGENASE 1 (EC 1.14.99.3) (HO-1) |
| H200006902 | TIEG | NM_005655 | AF050110 | TRANSFORMING GROWTH FACTOR-BETA-INDUCIBLE EARLY GROWTH RESPONSE PROTEIN 1 (TGFB-INDUCIBLE EARLY GROWTH RESPONSE PROTEIN 1) (TIEG-1) (KRUEPPEL-LIKE FACTOR 10) |
| H200001600 | NOTCH2 | NM_024408 | U77493 | NEUROGENIC LOCUS NOTCH HOMOLOG PROTEIN 2 PRECURSOR (NOTCH 2) (HN2) |
| H300007970 | ZFP36L1 | NM_004926 | BC018340 | BUTYRATE RESPONSE FACTOR 1 (TIS11B PROTEIN) (EGF-RESPONSE FACTOR 1) (ERF-1) |
| H300019724 | IFI30 | NM_006332 | AF097362 | GAMMA-INTERFERON INDUCIBLE LYSOSOMAL THIOL REDUCTASE PRECURSOR (GAMMA-INTERFERON-INDUCIBLE PROTEIN IP-30) |
| H200004653 | — | — | AB033073 | — |
| H300012785 | WARS | NM_004184 | X67928 | TRYPTOPHANYL-TRNA SYNTHETASE (EC 6.1.1.2) (TRYPTOPHAN--TRNA LIGASE) (TRPRS) (IFP53) (HWRS) |
| H200010704 | CPVL | NM_031311 | BC016838 | SERINE CARBOXYPEPTIDASE VITELLOGENIC-LIKE |
| H200017278 | SCO2 | NM_005138 | AL021683 | SCO2 PROTEIN HOMOLOG, MITOCHONDRIAL PRECURSOR |
| H200005078 | — | — | NM_006344 D50532 | MACROPHAGE LECTIN 2 (CALCIUM DEPENDENT) |

Summarizing, numerous studies now highlight the power of gene expression profiling to characterize the biological phenotype of complex diseases. The potential clinical utility of gene expression profiles has been shown in cancer research, in which the identification of patterns of gene expression within tumors has led to the characterization of tumor subtypes, prognostic categories and prediction of therapeutic response (Potti et al, N. Engl. J. Med. 355:570-580 (2006), Cheng et al, J. Clin. Oncol. 24:4594-4602 (2006), Potti et al, Nat. Med. 12:1294-1300 (2006), Nevins et al, Nat. Rev. Genet. 8:601-609 (2007), Alizadeh et al, Nature 403:503-511 (2000)). Beyond analysis of tumor tissues, it has also been suggested that gene expression profiling of the peripheral blood can provide indication of infections, cancer, heart disease, allograft rejection, environmental exposures and as a means of biological threat detection (Mandel et al, Lupus 15:451-456 (2006), Heller et al, Proc. Natl. Acad. Sci. USA 94:2150-2155 (1997), Edwards et al, Mol. Med. 13:40-58 (2007), Baird, Stroke 38:694-698 (2007), Rubins et al, Proc. Natl. Acad. Sci. USA 101:15190-15195 (2004), Martin et al, Proc. Natl. Acad. Sci. USA 98:2646-2651 (2001), Patino et al, Proc. Natl. Acad. Sci. USA 102:3423-3428 (2005), Lampe et al, Cancer Epidemiol. Biomarkers Prev. 13:445-453 (2004), Ramilo et al, Blood 109:2066-2077 (2007), Horwitz et al, Circulation 110:3815-3821 (2004), Lin et al, Clinic Chem. 49:1045-1049 (2003)). While the concept of PB cells as sentinels of disease is not new, it remains unclear whether PB gene expression profiles that have been associated with various conditions are specific for those diseases or rather reflect a common molecular response to a variety of genotoxic stresses. Given the dynamic nature of the cellular composition of PB blood (Whitney et al, Proc. Natl. Acad. Sci. USA 101:1896-1901 (2003)) and the complexity of cellular responses over time (Whitney et al, Proc. Natl. Acad. Sci. USA 101:1896-1901 (2003)), the durability of PB signatures over time is also uncertain and could affect the diagnostic utility of this approach for public health screening.

A purpose of the studies described above was to address the capacity for PB gene expression profiles to distinguish an environmental exposure, in this case ionizing radiation, versus other medical conditions and to examine the impact of time, gender and genotype on the accuracy of these profiles. It was found that PB gene expression signatures can be identified which accurately predict irradiated from non-irradiated mice and distinguish different levels of radiation exposure, all within a heterogeneous population with respect to gender, genotype and time from exposure. These results suggest the potential for PB gene expression profiling to be applied successfully in the screening for an environmental exposure. Previous studies have indicated that inter-individual variation in gene expression occurs within healthy individuals (Whitney et al, Proc. Natl. Acad. Sci. USA 101:1896-1901 (2003)) and may therefore limit the accuracy of PB gene expression profiling to detect diseases or exposures. The results provided here demonstrate that the environmental exposure tested here, ionizing radiation, induced a pronounced and characteristic alteration in PB gene expression such that a PB expression profile was highly predictive of radiation status in a population with variable gender, genotype and time of analysis. From a practical standpoint, these data suggest the potential utility of this approach for biodosimetric screening of a heterogeneous human population in the event of a purposeful or accidental radiological or nuclear event (Wasalenko et al, Ann. Int. Med. 140:1037-1051 (2004), Mettler et al, N. Engl. J. Med. 346:1554-1561 (2002), Dainiak, Exp. Hematol. 30:513-528 (2002)).

This study revealed that sex differences can impact the accuracy of this approach, particularly in distinguishing mice exposed to lower dose irradiation from non-irradiated controls. These results imply that aspects of the PB response to ionizing radiation are specified by sex-associated genes. Whitney et al (Proc. Natl. Acad. Sci. USA 101:1896-1901 (2003)) previously showed that sex differences were associated with variation in PB autosomal gene expression in healthy individuals. The instant study suggests that sex differences may contribute to characteristically distinct PB molecular responses to environmental stress (radiation) and the accuracy of PB gene expression profiling for medical screening can be affected by sex. These sex-related differences in PB response to ionizing radiation are perhaps illustrated by the fact that only 2 genes overlapped between the male and female PB signatures of 50 cGy (Ccng1 and Dda3).

Interestingly, differences in genotype did not significantly impact the accuracy of the PB gene expression signatures to distinguish radiation response such that PB signatures from C57Bl6 mice displayed 100% accuracy in predicting the status of BALB/c mice and vice versa. This observation demonstrates that, while genotype differences can account for some variation in PB gene expression (Whitney et al, Proc. Natl. Acad. Sci. USA 101:1896-1901 (2003)), the alterations in PB gene expression induced by 3 different levels of radiation exposure are such that PB expression profiling is highly accurate in distinguishing all irradiated mice across different genotypes. Very few genes were found in common between the 2 strains of mice at each level of radiation exposure, indicating that diverse sets of genes contribute to the PB response to radiation and that unique sets of genes can be identified which are predictive of radiation response.

The time of PB collection following radiation exposure had no significant impact on the accuracy of PB signatures to predict radiation status or distinguish different levels of exposure. First, the accuracy of PB signatures to predict radiation status and distinguish different levels of radiation exposure did not decay over time. Second, when we applied a PB signature from a single time point (6 hrs) against PB samples collected from mice at other time points (24 hr and 7 days), the accuracy of the prediction remained 100% in all cases. Therefore, time as a single variable did not lessen the accuracy of this approach to distinguish irradiated from non-irradiated animals. However, the content of the genes which comprised the PB signatures changed significantly as a function of time and <20% of the genes overlapped between the PB signatures of radiation at 6 hr, 24 hr, and 7 days. Taken together, these data indicate that PB predictors of radiation response do change over time, but PB signatures can continuously be identified through 7 days that are highly accurate at predicting radiation status and distinguishing different levels of radiation exposure. From a practical perspective, these results suggest that the application of a single reference set of "radiation response" genes would be unlikely to provide the most sensitive screen for radiation exposure over time. Conversely, reference lists of PB genes that are specific for different time points could be applied in the screening for radiation exposure provided that the time of exposure was known.

A critical question to be addressed in the development of PB gene expression profiling to detect medical conditions or exposures is the specificity of PB gene expression changes in response to genotoxic stresses. The PB signatures of 3 different doses of radiation displayed 100% accuracy in identifying septic animals as non-irradiated and the PB signature of sepsis was also 100% accurate in identifying irradiated mice as non-septic. These results demonstrate specificity in the PB responses to ionizing radiation and sepsis. These data also provide in vivo validation of a prior report by Boldrick et al (Proc. Natl. Acad. Sci. USA 99:972-977 (2002)) in which human PB mononuclear cells were found to have a stereotypic response to LPS exposure in vitro and specific alterations in gene expression were observed in response to different strains of bacteria (Boldrick et al, Proc. Natl. Acad. Sci. USA 99:972-977 (2002)). Ramilo et al. also recently reported that distinct patterns of PB gene expression can be identified among patients with different bacterial infections (Ramilo et al, Blood 109:2066-2077 (2007)). No genes were found to be in common between the PB signatures of radiation exposure and the PB signature of gram negative sepsis. Taken together, the results demonstrate that the in vivo PB molecular responses to ionizing radiation and bacterial sepsis are quite distinct and can be utilized to distinguish one condition from the other with a high level of accuracy.

The analyses of expression signatures in human patients demonstrated that it is possible to utilize PB gene expression profiles to distinguish individuals who have been exposed to an environmental hazard, ionizing radiation, within a heterogeneous human population with a high level of accuracy. It will be important to further test the accuracy of this PB predictor of human radiation exposure in a human population exposed to lower dose irradiation (e.g. 0.1-1 cGy), as might be expected via occupational exposures (e.g. radiology technicians, nuclear power plant workers) (Seierstad et al, Radiat. Prot. Dosimetry 123:246-249 (2007), Moore et al, Radiat. Res. 148:463-475 (1997), Einstein et al, Circulation 116:1290-1305 (2007)). A potential pitfall in the clinical application of PB gene expression profiling would be that variations in PB gene expression in people would be such that it might be difficult to distinguish the effects of a given exposure or medical condition from expected background alterations in gene expression (Whitney et al, Proc. Natl. Acad. Sci. USA 101:1896-1901 (2003)). However, Whitney et al (Proc. Natl. Acad. Sci. USA 101:1896-1901 (2003)) showed that the alterations in PB gene expression observed in patients with lymphoma or bacterial infection was significantly greater than the relatively narrow variation observed in healthy individuals (Whitney et al, Proc. Natl. Acad. Sci. USA 101:1896-1901 (2003)). This study confirms that PB gene expression profiles can be successfully applied to detect a specific exposure in a heterogeneous human population and that inter-individual differences in PB gene expression do not significantly confound the utility of this approach.

It was also shown that unique PB gene expression profiles can be identified which distinguish chemotherapy-treated patients versus patients who had not received chemotherapy with an overall accuracy of 81% and 78%, respectively. Similar to the PB signature of radiation, the PB signature of chemotherapy demonstrated accuracy and specificity in distinguishing healthy individuals and pre-irradiated patients (100% and 92% accuracy, respectively). However, the accuracy of the PB signature of chemotherapy was more limited when tested against patients who received radiation conditioning (62%). This observation provides the basis for further investigation as to which families of genes may be represented in both the PB molecular response to radiation and chemotherapy. However, since all 12 of the post-irradiation patients whose status was mispredicted by the PB chemotherapy signature had received combination chemotherapy within the prior year, the true specificity of this PB signature of chemotherapy cannot be addressed via this comparison. Additional patients are currently being enrolled to this study who have not undergone prior chemotherapy to further test the specificity of a PB metagene of chemotherapy treatment.

Peripheral blood is a readily accessible source of tissue which has the potential to provide a window to the presence of disease or exposures. Early studies applying PB gene expression analysis have demonstrated that this approach is sensitive for the detection of patterns of gene expression in association with a variety of medical conditions (Mandel et al, Lupus 15:451-456 (2006), Heller et al, Proc. Natl. Acad. Sci. USA 94:2150-2155 (1997), Edwards et al, Mol. Med. 13:40-58 (2007), Baird, Stroke 38:694-698 (2007), Rubins et al, Proc. Natl. Acad. Sci. USA 101:15190-15195 (2004), Martin et al, Proc. Natl. Acad. Sci. USA 98:2646-2651 (2001), Patino et al, Proc. Natl. Acad. Sci. USA 102:3423-3428 (2005), Lampe et al, Cancer Epidemiol. Biomarkers Prev. 13:445-453 (2004), Ramilo et al, Blood 109:2066-2077 (2007), Whitney et al, Proc. Natl. Acad. Sci. USA 101:1896-1901 (2003), Dressman et al, PLoS Med. 4:690-701 (2007)). It remains to be determined whether PB gene expression profiles can be successfully applied in medical practice or public health screening for the early detection of specific diseases or environmental exposures. The present results demonstrate that PB gene expression profiles can be identified in mice and humans which are specific, accurate over time, and not confounded by inter-individual differences.

All documents and other information sources cited above are hereby incorporated in their entirety by reference.

What is claimed is:

1. A method comprising:
   i) obtaining a blood sample from a human exposed to radiation,
   ii) isolating mononuclear cells from said blood sample,
   iii) extracting RNA from said mononuclear cells,
   iv) analyzing said RNA for expression of no more than 25 genes, wherein the no more than 25 genes are all of the genes set forth in Table 7, or wherein the no more than 25 genes comprise a subset of the genes set forth in Table 7 of at least 5 genes.

2. The method according to claim 1 wherein said blood sample is a peripheral blood sample.

3. The method according to claim 1 wherein said blood sample is obtained within 7 days of exposure of said individual to radiation.

4. The method according to claim 1 wherein said blood sample is obtained at about 24-168 hours after exposure of said individual to radiation.

5. The method according to claim 1 wherein said RNA is analyzed for expression of H200000088, H200008365, H200011577, H200014719, H200016323, H300000421, H300003103, H300010830, H300015667, H300019371, H300020858, H300021118 and H300022025.

6. The method according to claim 1 wherein said subset comprises at least 10 of said genes set forth in Table 7.

7. The method according to claim 1 wherein said extracted RNA resulting from step (iii) is amplified.

8. The method according to claim 1 wherein step (iv) is effected using a microarray technique.

9. The method according to claim 1 wherein said subset comprises BBC3, BAX, CDKN1A, DDB2, and PCNA.

10. A method comprising:
    i) obtaining a blood sample from a human exposed to radiation, and
    ii) analyzing RNA in the blood sample for expression of no more than 25 genes, wherein the no more than 25 genes are all of the genes set forth in Table 7, or wherein the no more than 25 genes comprise a subset of the genes set forth in Table 7 of at least 5 genes.

11. The method according to claim 10 wherein said subset comprises BBC3, BAX, CDKN1A, DDB2, and PCNA.

12. The method according to claim 10 wherein said blood sample is obtained within 7 days of exposure of said individual to radiation.

13. The method according to claim 10 wherein said blood sample is obtained at about 24-168 hours after exposure of said individual to radiation.

* * * * *